(12) United States Patent
Gautier et al.

(10) Patent No.: US 12,084,608 B2
(45) Date of Patent: Sep. 10, 2024

(54) LOW-DIMENSIONAL HYBRID POST-PEROVSKITES FOR HIGH EFFICIENCY WHITE-LIGHT EMISSION

(71) Applicants: Centre National de la Recherche Scientifique, Paris (FR); Université de Nantes, Nantes (FR)

(72) Inventors: Romain Gautier, Nantes (FR); Florian Massuyeau, Sainte Luce sur Loire (FR); Michael Paris, Cugand (FR)

(73) Assignees: CENTRE NATIONAL DE LA RECHERCHE SCIENTIFIQUE, Paris (FR); UNIVERSITE DE NANTES, Nantes (FR)

( * ) Notice: Subject to any disclaimer, the term of this patent is extended or adjusted under 35 U.S.C. 154(b) by 796 days.

(21) Appl. No.: 17/052,887

(22) PCT Filed: Jun. 14, 2019

(86) PCT No.: PCT/EP2019/065770
§ 371 (c)(1),
(2) Date: Nov. 4, 2020

(87) PCT Pub. No.: WO2019/238960
PCT Pub. Date: Dec. 19, 2019

(65) Prior Publication Data
US 2021/0071075 A1    Mar. 11, 2021

(30) Foreign Application Priority Data
Jun. 15, 2018 (EP) .................................. 18305737

(51) Int. Cl.
| | | |
|---|---|---|
| *C09K 11/06* | (2006.01) | |
| *C07F 7/24* | (2006.01) | |
| *H01L 33/50* | (2010.01) | |
| *H10K 85/30* | (2023.01) | |
| *B82Y 20/00* | (2011.01) | |
| *B82Y 40/00* | (2011.01) | |

(52) U.S. Cl.
CPC ................ *C09K 11/06* (2013.01); *C07F 7/24* (2013.01); *H01L 33/502* (2013.01); *H10K 85/30* (2023.02); *B82Y 20/00* (2013.01); *B82Y 40/00* (2013.01); *C09K 2211/1044* (2013.01); *C09K 2211/188* (2013.01)

(58) Field of Classification Search
CPC ............ C09K 11/06; C09K 2211/1044; C09K 2211/188; C07F 7/24; H01L 33/502; H10K 85/30; H10K 50/11; B82Y 20/00; B82Y 40/00; C07D 295/02
USPC ....................................................... 544/225
See application file for complete search history.

(56) References Cited

FOREIGN PATENT DOCUMENTS

EP    122291 A2    8/2001

OTHER PUBLICATIONS

Gautier, Romain, Towards magnetic or luminescent halide materials synthesized under hydrothermal conditions, Abstracts of Papers, 250th ACS National Meeting & Exposition, Boston, MA, United States, Aug. 16-20, 2015 (2015), INOR-281. American Chemical Society: Washington, D., p. 1 (Year: 2015).*
A. Leguy, A. M. et al. Experimental and theoretical optical properties of methylammonium lead halide perovskites. Nanoscale 8, 6317-6327 (2016).
Anicete-Santos, M. et al. Contribution of structural order-disorder to the green photoluminescence of PbWO4. Phys. Rev. B 75, 165105 (2007).
Authier, A. International Tables for Crystallography 2nd edn, vol. D, Ch. A.A (Wiley, 2013).
Bischof, C., Wahsner, J., Scholten, J., Trosien, S. & Seitz, M. Quantification of C-H Quenching in Near-IR Luminescent Ytterbium and Neodymium Cryptates. J. Am. Chem. Soc. 132, 14334-14335 (2010).
Blancon, J.-C. et al. Extremely efficient internal exciton dissociation through edge states in layered 2D perovskites. Science eaal4211 (2017). doi:10.1126/science.aal4211.
Chayen, N. E. & Saridakis, E. Protein crystallization: from purified protein to diffraction-quality crystal. Nat. Methods 5, 147-153 (2008).
Cortecchia, D. et al. Broadband Emission in Two-Dimensional Hybrid Perovskites: The Role of Structural Deformation, J. Am. Chem. Soc. 139, 39-42 (2017).
Cortecchia, D. et al. Polaron self-localization in white-light emitting hybrid perovskites. J. Mater. Chem. C 5, 2771-2780 (2017).
De Gruijter, W. C. & Kerssen, J. EPR and luminescence of u.v. irradiated PbCl2 and PbBr2 crystals. Solid State Commun. 10, 837-841 (1972).
De Mello, J. C., Wittmann, H. F. & Friend, R. H. An improved experimental determination of external photoluminescence quantum efficiency. Adv. Mater. 9, 230-232 (1997).
Dobson, D. P. et al. Towards better analogues for MgSiO3 post-perovskite: NaCoF3 and NaNiF3, two new recoverable fluoride post-perovskites. Physics of the Earth and Planetary Interiors, 189, 3-4, 171-175 (2011).
Dohner, E. R., Hoke, E. T. & Karunadasa, H. I. Self-Assembly of Broadband White-Light Emitters. J. Am. Chem. Soc. 136, 1718-1721 (2014).

(Continued)

*Primary Examiner* — Taylor V Oh
(74) *Attorney, Agent, or Firm* — ICANTOR COLBURN LLP

(57) ABSTRACT

The present invention relates to a new type of low-dimensional hybrid post-perovskites for high efficiency white light emission. More precisely, the invention relates to a one dimensional post-perovskite of formula $A_aM_mX_x \cdot yH_2O$ wherein A is a cis- or trans-2,5-dialkylpiperazine derivative bearing $C_1$-$C_3$ linear or branched alkyl groups, M is one or more metal, X one or more halogen, $0<a<5$, $1<m<2$, $2<x<12$, $0<y$. The invention also relates to material and luminescent device comprising the same and methods of preparation of the of low-dimensional hybrid post-perovskites.

23 Claims, 14 Drawing Sheets

(56) References Cited

OTHER PUBLICATIONS

Dohner, E. R., Jaffe, A., Bradshaw, L. R. & Karunadasa, H. I. Intrinsic White-Light Emission from Layered Hybrid Perovskites. J. Am. Chem. Soc. 136, 13154-13157 (2014).

Frisch, M. et al. Gaussian, Inc., Wallingford CT, 2016. Gaussian G16A03. 2016.

Handbook of Crystal Growth (Second Edition). in (ed. Nishinaga, T.) iii (Elsevier, 2015). doi:10.1016/B978-0-444-56369-9.01001-7.

Hu, T. et al. Mechanism for Broadband White-Light Emission from Two-Dimensional (110) Hybrid Perovskites. J. Phys. Chem. Lett. 7, 2258-2263 (2016).

Iwanaga, M., Watanabe, M. & Hayashi, T. Charge separation of excitons and the radiative recombination process in $PbBr_2$ crystals. Phys. Rev. B 62, 10766-10773 (2000).

Li, Y. Y. et al. Novel <110>-Oriented Organic-Inorganic Perovskite Compound Stabilized by N-(3-Aminopropyl) imidazole with Improved Optical Properties. Chem. Mater. 18, 3463-3469 (2006).

Llao, W.-Q. et al. A lead-halide perovskite molecular ferroelectric semiconductor. Nat. Commun. 6, 8338 (2015).

Mao, L., Wu, Y., Stoumpos, C. C., Wasielewski, M. R. & Kanatzidis, M. G. White-Light Emission and Structural Distortion in New Corrugated Two-Dimensional Lead Bromide Perovskites. J. Am. Chem. Soc. 139, 5210-5215 (2017).

Massuyeau, F. et al. Electronic interaction in composites of a conjugated polymer and carbon nanotubes: first-principles calculation and photophysical approaches. Beilstein J. Nanotechnol. 6, 1138-1144 (2015).

Mitzi, D. B., Wang, S., Feild, C. A., Chess, C. A. & Guloy, A. M. Conducting Layered Organic-inorganic Halides Containing <110>-Oriented Perovskite Sheets. Science 267, 1473-1476 (1995).

Nie, W. et al. High-efficiency solution-processed perovskite solar cells with millimeter-scale grains. Science 347, 522-525 (2015).

Saidaminov, M. I. et al. High-quality bulk hybrid perovskite single crystals within minutes by inverse temperature crystallization. Nat. Commun. 6, 8586 (2015).

Shi, D. et al. Low trap-state density and long carrier diffusion in organolead trihalide perovskite single crystals. Science 347, 519-522 (2015).

Smith, M. D., Jaffe, A., Dohner, E. R., Lindenberg, A. & Karunadasa, H. I. Structural Origins of Broadband Emission from Layered Pb—Br Hybrid Perovskites. Chem. Sci. 8, 4497-4504 (2017).

Song, K. S. & Williams, R. T. Self-Trapped Excitons, (Springer-Verlag, 1993).

Stranks, S. D. & Snaith, H. J. Metal-halide perovskites for photovoltaic and light-emitting devices. Nat. Nanotechnol. 10, 391-402 (2015).

Sutherland, B. R. & Sargent, E. H. Perovskite photonic sources. Nat. Photonics 10, 295-302 (2016).

Takeoka, Y., Asai, K., Rikukawa, M. & Sanui, K. Hydrothermal Synthesis and Structure of Zero-dimensional Organic-inorganic Perovskites. Chem. Lett. 34, 602-603 (2005).

Tan, Z.-K. et al. Bright light-emitting diodes based on organometal halide perovskite. Nat. Nanotechnol. 9, 687-692 (2014).

Thirumal, K. et al. Morphology-Independent Stable White-Light Emission from Self-Assembled Two-Dimensional Perovskites Driven by Strong Exciton-Phonon Coupling to the Organic Framework. Chem. Mater. 29, 3947-3953 (2017).

Tsai, H. et al. High-efficiency two-dimensional Ruddlesden-Popper perovskite solar cells. Nature 536, 312-316 (2016).

Tulsky, E. G. & Long, J. R. Dimensional Reduction: A Practical Formalism for Manipulating Solid Structures. Chem. Mater. 13, 1149-1166 (2001).

Wang, S.-S. et al. Temperature-Induced Structural Phase Transitions in Two New Postperovskite Coordination Polymers. Crystal Growth & Design, 19, 2, 1111-1117 (2019).

Wolbers, M. P. O. et al. Photophysical studies of m-terphenyl-sensitized visible and near-infrared emission from organic 1:1 lanthanide ion complexes in methanol solutions. J. Chem. Soc. Perkin Trans. II 1998, 2141-2150 (1998).

Wu, X. et al. Trap States in Lead Iodide Perovskites. J. Am. Chem. Soc. 137, 2089-2096 (2015).

Xie, L.-Q. et al. Organic-inorganic interactions of single crystalline organolead halide perovskites studied by Raman spectroscopy. Phys. Chem. Chem. Phys. 18, 18112-18118 (2016).

Yanal, T., Tew, D. P. & Handy, N. C. A new hybrid exchange-correlation functional using the Coulomb-attenuating method (CAM-B3LYP). Chem. Phys. Lett. 393, 51-57 (2004).

Yangul, A. et al. Optical Investigation of Broadband White-Light Emission in Self-Assembled Organic-Inorganic Perovskite $(C_6H_{11}NH_3)_2PbBr_4$. J. Phys. Chem. C 119, 23638-23647 (2015).

Yin, J., Li, H., Cortecchia, D., Soci, C. & Brédas, J.-L. Excitonic and Polaronic Properties of 2D Hybrid Organic-Inorganic Perovskites. ACS Energy Lett. 2, 417-423 (2017).

Yuan, M. et al. Perovskite energy funnels for efficient light-emitting diodes. Nat. Nanotechnol. 11, 872-877 (2016).

Yuan, Z. et al. One-dimensional organic lead halide perovskites with efficient bluish white-light emission. Nat. Commun. 8, 14051 (2017).

Zhang, Z., Wang, M., Ren, L. & Jin, K. Tunability of Band Gap and Photoluminescence in $CH_3NH_3PbI_3$ Films by Anodized Aluminum Oxide Templates. Sci. Rep. 7, 1918 (2017).

Zhuang, Z. et al. Intrinsic Broadband White-Light Emission from Ultrastable, Cationic Lead Halide Layered Materials. Angew. Chem. 129, 14603-14608 (2017).

Anna Bonamartini, "An Additional Structural and Electrical Study of Polymeric Haloplumbates (II) with Hetercyclic Diprotonated Amines", Inorganic Chemistry, vol. 40, No. 2, Jan. 1, 2001, pp. 218-223, XP055510847.

Essid Manel;, "Synthesis, characterization and antioxidant activity of a novel organic-inorganic hybrid materialtrans-2,5-dimethylpiperazine-1, 4-diium pentachlorobosmuthate (III):{C6H16N2} BiC15". Journal of Molecular Structure, vol. 1117, Mar. 18, 2016, pp. 257-264, XP029523544.

International Search Report for corresponding application PCT/EP2019/065770 filed Dec. 14, 2019; Mail date Jul. 30, 2019.

Qin Hou, "New organically templated chained and layered iodoplumbates" Crystengcomm, vol. 14, No. 11, )Jan. 1, 2012, p. 4000, XP055510878.

Written Opinion of the International Searching Authority for corresponding application PCT/EP2019/065770 filed Dec. 14, 2019; Mail date Jul. 30, 2019.

Yu Peng, et al; "White-light emission in a chiral one-dimensional organic-inorganic hybrid perovskite", Journal of Materials Chemistry C, May 2, 2018, pp. 6033-6037, XP055510884.

* cited by examiner a b

LOW-DIMENSIONAL HYBRID POST-PEROVSKITES FOR HIGH EFFICIENCY WHITE-LIGHT EMISSION

TECHNICAL FIELD

The present invention relates to a new type of low-dimensional hybrid post-perovskites for high efficiency white light emission. More precisely, the invention relates to a one dimensional post-perovskite of formula $A_aM_mX_x$, $yH_2O$ wherein A is a cis- or trans-2,5-dialkylpiperazine derivative bearing $C_1$-$C_3$ linear or branched alkyl groups, M is one or more metal, X one or more halogen, $0<a\le5$, $1\le m\le2$, $2\le x\le12$, $0\le y$. The invention also relates to material and luminescent device comprising the same and methods of preparation of the of low-dimensional hybrid post-perovskites.

In the following description, references are mentioned in ([ ]) which is linked to the list at the end of the examples.

TECHNICAL BACKGROUND

Low-dimensional hybrid perovskites have recently shown a great potential for applications in solar cells and light-emitting diodes [1-7]. While decreasing the dimensionality, such compound exhibit quantum confinement effects leading to tunable optical and electronic properties. Thus, broadband white-light emission has been observed from diverse hybrid perovskites and, owing to high color rendering index (CRI), high thermal stability, and low-temperature solution processability, this family of materials has focused interest for solid-state lighting.

Mechanisms for optoelectronic properties of hybrid perovskites have been widely investigated in the past few years. The photogeneration of electron-hole pairs is highly efficient and, for this reason, these materials are of interest for applications ranging from photovoltaics to solid-state lighting. However, after the photogeneration of excitons, specific mechanisms must be enhanced depending on the targeted properties. On the one hand, the exciton dissociation and the diffusion of free carriers must be optimal when considering solar cells [4, 5, 14, 15]. On the other hand, when considering solid-state lighting, the broadband white emission was proposed to originate from exciton self-trapping forming radiative centres identified by first-principle calculations as $Pb_2^{3+}$, $Pb^{3+}$, $X_2^-$ and $X^{2-}$ (X=Halogens) [10, 16-19].

However, the reported photoluminescence quantum yields (PLQY) remain low (i.e. PLQY in the range 0.5%-9%) and no approach has shown to successfully increase the intensity of this emission [8-13].

There is therefore a need to enhance the photoluminescence quantum yields of hybrid perovskites and more generally the optoelectronic properties of hybrid perovskites known in the art.

DETAILED DESCRIPTION

Applicants have surprisingly observed that, compared to the prior art 2D perovskite, the photoluminescence quantum yields can be greatly increased by changing those for one dimensional (1D) hybrid post-perovskite.

Applicants demonstrated that this white emission can be greatly enhanced for a polymorph of the 2D hybrid perovskite: the 1D hybrid post-perovskite of the invention which shows a PLQY of $\ge 10\%$, preferably $\ge 20\%$, $\ge 30\%$ or even $\ge 45\%$. This new family of hybrid metal halide materials can enhance all the properties requiring the stabilization of trapped excitons.

The invention relates to one dimensional (1D) hybrid post-perovskite of formula I:

$$A_aM_mX_x,yH_2O \qquad \text{Formula I}$$

wherein
$0<a\le5$,
$1\le m\le2$,
$2\le x\le12$,
$0\le y$,
A represents a cis- or trans-piperazine derivative of formula II:

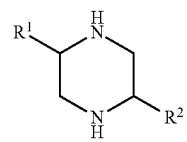

Formula II in which $R^1$ and $R^2$, identical or different, represent a $C_1$-$C_3$ linear or branched alkyl chain,
M represents one or more metal atoms chosen from the group comprising Pb, Sn, Ge, Sb, Bi, Cu, Mn and Zn and mixture thereof,
X represents one or more halogen atoms.

Using the same approach to define "low-dimensional hybrid perovskite" from a "hybrid perovskite", the ladder compound of the invention is defined as a "low dimensional hybrid post-perovskite". The specific "ladder" structure of the compound of the invention can thus be considered as a low-dimensional hybrid post-perovskite. The 1D post-perovskites of the invention are built of both corner- and edge-sharing octahedral, hence the term "ladder". Therefore, as used herein, the term "ladder" refers to the typical structure of the 1D hybrid post-perovskite structure according to the invention wherein the octahedra are connected to each other through corners and edges instead of only corners like it is generally observed for 2D perovskites (differences are shown on FIGS. 1a and 1b).

The structure "post-perovskite" was originally assigned to the high-pressure phase of $MgSiO_3$. However, in the past years, the terminology "post-perovskite" has been extended to describe metal halides [49] or hybrid organic-inorganic compounds under atmospheric pressure [50]. Here, we extend the terminology to "low-dimensional post-perovskite".

The ladder compound of the invention could also be referenced as "one dimensional ladder structured hybrid metal halide".

It is thus meant by "one dimensional", the ladder structure of the post-perovskite according to the invention where the metal-halide moieties form one dimensional chains.

Advantageously, A may represent a cis- or trans-piperazine derivative of formula II:

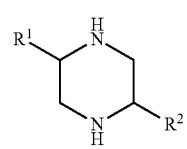

Formula II in which $R^1$ and $R^2$, identical or different, represent a $C_1$-$C_3$ linear or branched alkyl chain. Preferably, $R^1$ and $R^2$ represent methyl, ethyl, propyl or isopropyl groups and more preferably methyl groups. Preferably, A represents trans-2,5-dimethylpiperazine (TDMP).

Advantageously, X may represent one or more halogen atoms. The halogen may be independently chosen from F, Cl, Br, and I and mixtures thereof. X may be a mixture of two or more halogens F, Cl, Br, and/or I. Preferably, X may be Cl, Br, and/or I.

Advantageously, the one dimensional (1D) hybrid post-perovskite of the invention may be of formula III:

$$A_a M_m Br_b Cl_c I_i, yH_2O \qquad \text{Formula III}$$

wherein

A, a, M, m and y are defined as above, $0 \leq b \leq 12$, $0 \leq c \leq 12$, $0 \leq i \leq 12$ and $2 \leq b+c+i \leq 12$.

Advantageously, M may represent one or more metal atoms. The metal may be a metal chosen in the group comprising Pb, Sn, Ge, Sb, Bi, Cu, Mn and Zn. Preferably, the M may be Pb and/or Sn. Other metals not listed above may also be present in the one dimensional hybrid post-perovskite of the invention. For example, M may be Pb or Sn or M may represent a mixture of two or more metals wherein Pb represents at least 20 mol % of the mixture of metals M. M may be a mixture of metals $M^1$ and $M^2$, and $M^1$ and $M^2$ identical or different, may independently represent any metal M as defined as above.

Advantageously, the one dimensional (1D) hybrid post-perovskite of the invention may be of formula IV:

$$A_a M^1_{m1} M^2_{m2} Br_b Cl_c I_i, yH_2O \qquad \text{Formula IV}$$

wherein

A, a, b, c, i and y are defined as above, $M^1$ and $M^2$ identical or different, independently represents any metal M as defined as above, $0 \leq m1 \leq 2$, $0 \leq m2 \leq 2$ and $1 \leq m1+m2 \leq 2$.

Advantageously, a, x, m, b, c, i, m1 and m2 have the values given above. Preferably, a may range from 0 to 5 (0 being excluded), $0<a \leq 5$, preferably a=1.

Advantageously, m may range from 1 to 2, $1 \leq m \leq 2$, preferably m=1.

Advantageously, x may range from 2 to 12, $2 \leq x \leq 12$, preferably x=4.

Advantageously, b, c and i may each range from 0 to 12 and b+c+i=x and may range from 2 to 12.

Advantageously, m1 and m2 may each range from 0 to 2 and m1+m2=m and may range from 1 to 2.

Advantageously, a may be equal to 1, m may be equal to 1, x may be equal to 4, A may be TDMP, M may be Pb or Sn, and X may be Cl, Br, and/or I.

Advantageously, a may be equal to 1, m1 may be in a range from 0.9000 to 0.9999, m2 may be in a range from 0.0001 to 0.1000, x may be equal to 4, A may be TDMP, $M^1$ may be Pb or Sn, $M^2$ may be Mn and X may be Cl, Br, and/or I.

In a variant of the invention, it also relates to a one dimensional (1D) hybrid post-perovskite crystal form (i.e. (TDMP)PbBr$_4$) wherein the XRPD pattern at Bragg angles shows peaks of value (2θ) 7.92°, 12.52°, 14.60°, 20.24°, 22.50°, 23.20°, 28.22°, 28.80°.

In a variant of the invention, it also relates to a one dimensional (1D) hybrid post-perovskite crystal form (i.e. (TDMP)PbCl$_4$) wherein the XRPD pattern at Bragg angles shows peaks of value (2θ) 8.15°, 12.86°, 18.18°, 20.74°, 23.02°, 23.75°, 28.87°, 29.45°, 32.75°, 33.78°, 34.78°, 35.28°.

In a variant of the invention, it also relates to a one dimensional (1D) hybrid post-perovskite crystal form (i.e. (TDMP)PbI$_4$) wherein the XRPD pattern at Bragg angles shows peaks of value (2θ) 7.68°, 12.13°, 13.73°, 21.74°, 22.42°, 27.79°, 32.83°.

In a variant of the invention, it also relates to a one dimensional (1D) hybrid post-perovskite crystal form (i.e. (TDMP)Pb$_{0.9997}$Mn$_{0.0003}$Br$_4$) wherein the XRPD pattern at Bragg angles shows peaks of value (2θ) 8.10°, 12.71°, 20.45°, 22.68°, 23.40°, 28.40°, 28.98°.

The invention also relates to a method for producing one dimensional hybrid post-perovskite according to the invention, comprising a step of mixing the reagents:

one or more M or MX$_2$, a piperazine derivative, and one or more aqueous HX to obtain an aqueous mixture.

The piperazine derivative, M and X are defined as above.

Advantageously, the method further comprises a step of heating and agitating the mixture. The heating temperature may be from 20° C. to 250° C., preferably heating under reflux temperature, for example at 100° C. The agitation may be carried over a period from 10 seconds to 100 hours, preferably until complete dissolution of the metal, for example 8 hours.

The invention also relates to a luminescent material comprising a one dimensional hybrid post-perovskite according to the invention. It is meant by "luminescent material", a material capable of emitting light by a substance not resulting from heat; it is thus a form of cold-body radiation. It can be caused by chemical reactions, light, electrical energy, subatomic motions or stress on a crystal, which all are ultimately caused by spontaneous emission. This distinguishes luminescence from incandescence, which is light emitted by a substance as a result of heating.

The invention further relates to a luminescent device comprising a one dimensional hybrid post-perovskite material according to the invention. It is meant by "luminescent device", a device including a luminescent material.

The invention also concerns a use of a one dimensional hybrid post-perovskite according to the invention in a luminescent device. Examples of device include, but are not limited to, a device comprising LEDs such as a display or a backlighting unit, a LASER, a wireless light fidelity, a large area display.

The one dimensional hybrid post-perovskites of the invention have many advantages. In addition to the simple and reproducible synthesis conditions, the compounds of the invention may be soluble in water at room temperature under agitation, and films can be simply processed by drop casting technique.

Advantageously, the one dimensional hybrid post-perovskites of the invention may have the same structure, independently of the halogen used.

Advantageously, the one dimensional hybrid post-perovskites of the invention have a photoluminescence quantum yield superior or equal to 10%, preferably superior or equal to 20%, superior or equal to 30% or superior or equal to 45%. In the context of the invention, it is meant by "photoluminescence quantum yield", the ratio of the number of photons emitted to the number of photons absorbed by the sample at a certain excitation wavelength.

Advantageously, the material of the invention may be stable up to 250° C. which is higher than temperatures of use in LED technologies.

Other advantages may be observed by the skilled artisan upon reading the following examples.

EXAMPLES

Example 1: Materials and Methods

Materials Synthesis.

Polycrystalline samples were prepared by heating (reflux, about 100° C.) under agitation, a mixture of 4.82 mmol Pb metal (Alfa Aesar, 99.95%), 9.24 mmol Trans-2,5-dimethylpiperazine (Alfa Aeasar, 98%) or 4.86 mmol 1,4-Bis(3-aminopropyl)piperazine, (Sigma Aldrich, 99%) with 20 ml of HBr (Alfa Aeasar, 48%).

After 24 hours, the solutions were cooled down, and the white precipitates were recovered by filtration and washed with ethanol.

A 1D post-perovskite of formula (TDMP)PbBr$_4$ according to the invention was obtained.

1D post-perovskites of formula (TDMP)PbCl$_4$ and (TDMP)PbI$_4$ according to the invention were obtained according to the same procedure.

A comparative example 2D perovskite of formula (BAPP)Pb$_2$Br$_8$ has been prepared in the same experimental conditions. (BAPP)Pb$_2$Br$_8$ is not part of the invention.

Figure 14:
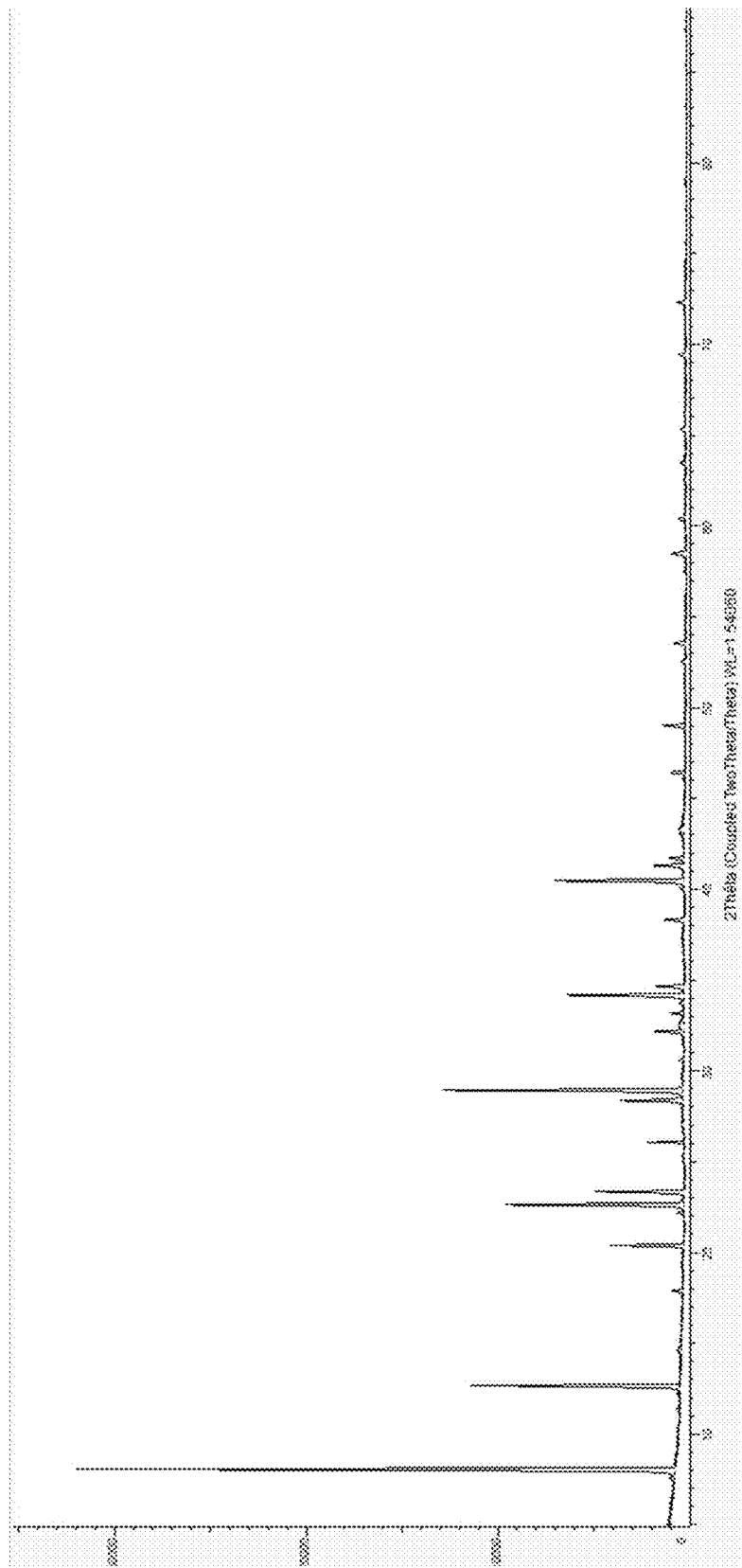
FIG. 14 represents the powder X-ray diffraction of (TDMP)Pb$_{0.9997}$Mn$_{0.0003}$Br$_4$.
Figure 15:
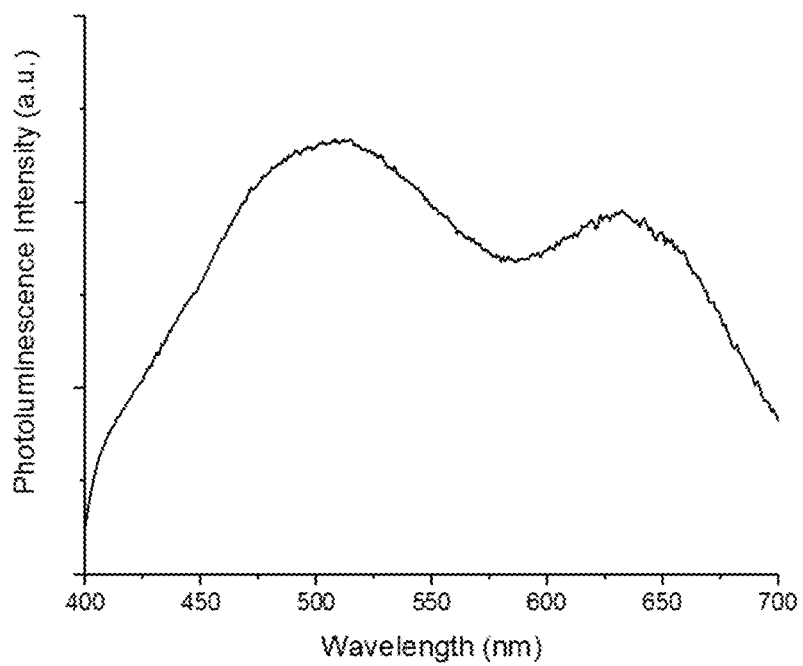
FIG. 15 represents the photoluminescence spectrum of (TDMP)Pb$_{0.9997}$Mn$_{0.0003}$Br$_4$ at $\lambda_{exc}$=370 nm.
Figure 16:
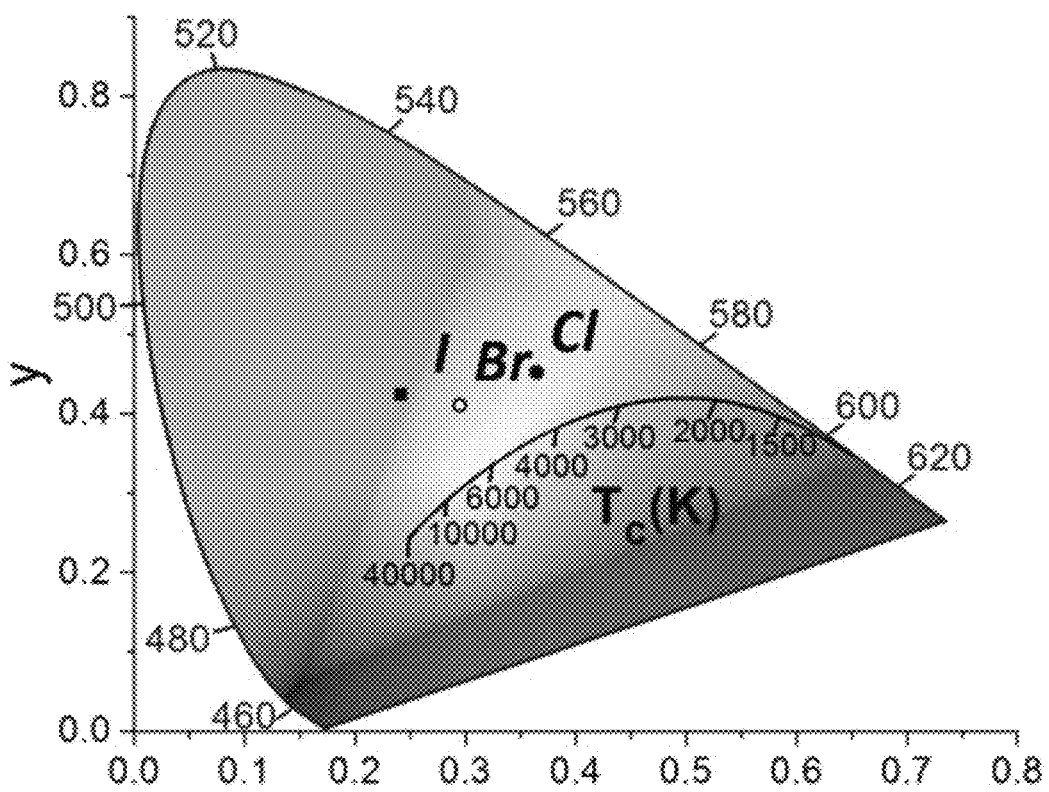
FIG. 16 represents the CIE coordinates for the series of lead halides (TDMP)PbX$_4$, wherein X is either I(■), Br(○) or Cl(●).

In other experiments, Mn partially substitutes the Pb in (TDMP)PbBr$_4$. (TDMP)Pb$_{0.9997}$Mn$_{0.0003}$Br$_4$ was prepared according to the same procedure as above but using 4.43 mmol Pb metal and 0.39 mmol MnO. The corresponding powder X-ray diffraction pattern and the emission spectrum are visible on FIGS. 14 and 15). An additional emission in the red region is observed. Thus, the correlated colour temperature (CCT) can be tuned and colour rendering indexes as high as 96 can be reached.

Single crystals were synthesized by hydrothermal method (180° C. during 24 h and slow cooling at the rate 10° C./h) using a 23 mL Teflon-lined stainless steel autoclave. For the 1D post-perovskite, larger crystals suitable for single-crystal X-ray diffraction could be grown by slow evaporation or vapour diffusion (i.e. diffusion of the vapour of a non-solvent (ethanol) inside of a vial containing the material dissolved in a solvent (water)) [34-36]. Crystals were recovered by filtration.

Single-Crystal X-Ray Diffraction.

The structure determination was carried out using a Bruker Nonius KappaCCD diffractometer (Mo Kα radiation). SADABS program was used for absorption corrections. The crystal structure was determined with SHELXT and refined with SHELXL-2013. PLATON program was used to check for additional symmetry elements. CCDC 1551179 contains the supplementary crystallographic data.

Thermal Analysis.

Differential scanning calorimetry and thermogravimetry were carried out simultaneously with a Netzsch STA 449F3 from room temperature to 800° C. under air (Ramp: 5° C./min).

Solid-State NMR.

$^{207}$Pb solid state NMR experiments were performed at 302 K on a 300 MHz Bruker Avance III by using a 4 mm MAS probe. The $^{207}$Pb MAS NMR spectra were acquired with a rotor synchronized Hahn echo sequence ($\pi/2$-$\tau$-$\pi$-$\tau$-acq) with $\tau$ equal to one rotor period and a radio-frequency field of 90 kHz. The MAS frequency was set to 14 kHz and the recycle delays between scans ranged from 2 to 5 s. Chemical shifts were referenced to Pb(CH$_3$)$_4$ at 0 ppm using a 0.5 M aqueous Pb(NO$_3$)$_2$ solution as a secondary reference ($\delta$=−2941 ppm from Pb(CH$_3$)$_4$).

Steady-State Photoluminescence.

All measurements were carried out on a Horiba Jobin-Yvon Flurolog 3 equipped with a 450 W xenon lamp. Two dimensional Excitation vs. emission contour maps were obtained with a CCD camera. Photoluminescence (PL) and photoluminescence excitation (PLE) spectra were acquired by means of R928 PMT detector. Samples were placed in an Oxford cryostat for cooling down to 77K. Photoluminescence Quantum Yield (PLQY) were achieved using the de Mello method [37]. To ensure the quality of the measurements, PLQY of standard samples were measured. SGA 550 100 Isiphor® powder from Sigma Aldrich was used and PLQYs of 93% was obtained. Homemade synthesized 2D EDBE-hybrid perovskite lead to a PLQY of 7% (close to the referenced one at 9%). The error on the PLQY measurements was estimated to be +/−5%.

Time-Resolved Photoluminescence.

Excitation is provided by a regenerative amplified femtosecond Ti:Sapphire laser system (Spectra Physics Hurricane X) frequency-tripled to obtain $\lambda_{exc}$=267 nm (pump fluence=30 µJ/cm$^2$). The transient signals were spectrally dispersed into a Princeton Instruments SP2300 imaging Acton spectrograph and temporally resolved with a high dynamic range Hamamatsu C7700 streak camera. Measurements were carried out in an Oxford cryostat for temperature measurement down to 77K (nitrogen cooling).

Raman Spectroscopy.

Raman spectra were acquired with $\lambda_{exc}$=660 nm from a Cobolt CW laser, at room temperature, using a Horiba Jobin-Yvon T64000 Raman.

UV/Vis Spectroscopy.

Optical reflection spectra were acquired using a Perkin lambda 1050 equipped with a 150 mm integrating sphere. Kubelka-Munk is obtained using the relation: $(1-R)^2/2R$ where R is the reflectance.

ICP OES.

The quantification of Mn was carried out using an ICP-OES iCAP6300 (Thermo). Five standards from 0.01 ppm to 1 ppm Mn were prepared. 100 mg of the material was dissolved into 10 mL of ultrapure water.

Example 2: Results

The 2D (110) hybrid perovskite exhibits structure in which the ammonium groups are placed within the cavities formed by the inorganic layers (FIG. 1(a)). The 1D hybrid post-perovskite (TDMP)PbBr$_4$ exhibits an intense white emission (FIG. 1(c)).

Figure 3:
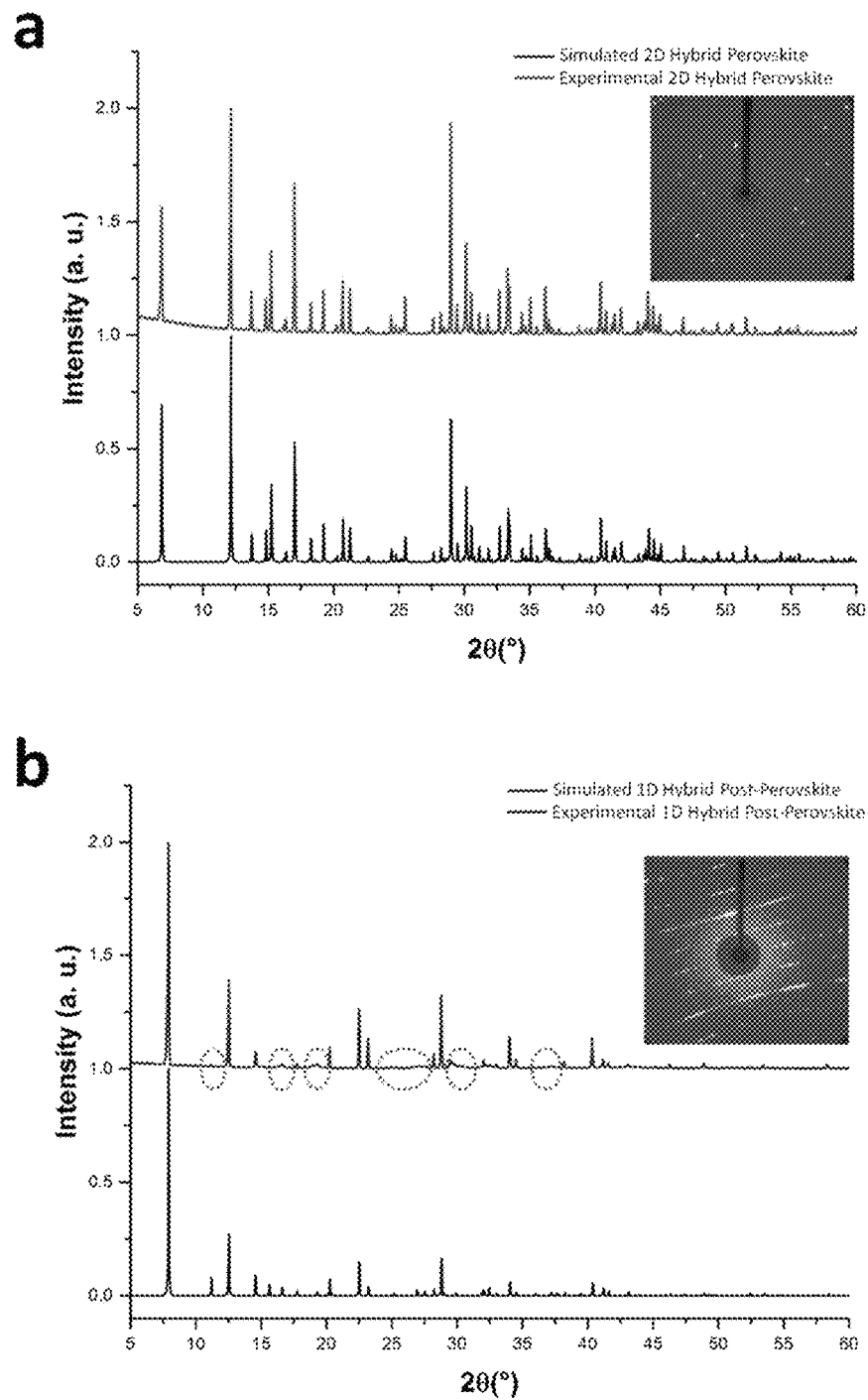
FIG. 3 represents powder X-Ray diffraction patterns of (a) layered 2D hybrid perovskite based on 1,4-Bis(3-aminopropyl)piperazine (BAPP) and (b) 1D hybrid post-perovskite based on trans-2,5-dimethylpiperazine (TDMP) (each bottom diagrams are simulations). In the case of 1D hybrid post-perovskite, diffuse scattering is observed in both powder X-ray diffraction patterns (dotted areas) and single-crystal X-ray diffraction data (inset).

X-Ray diffraction on single-crystals grown by slow evaporation or vapor diffusion as well as powder X-ray diffraction showed important diffuse scattering which is characteristic of a strong structural disorder (FIG. 3).

Figure 4:
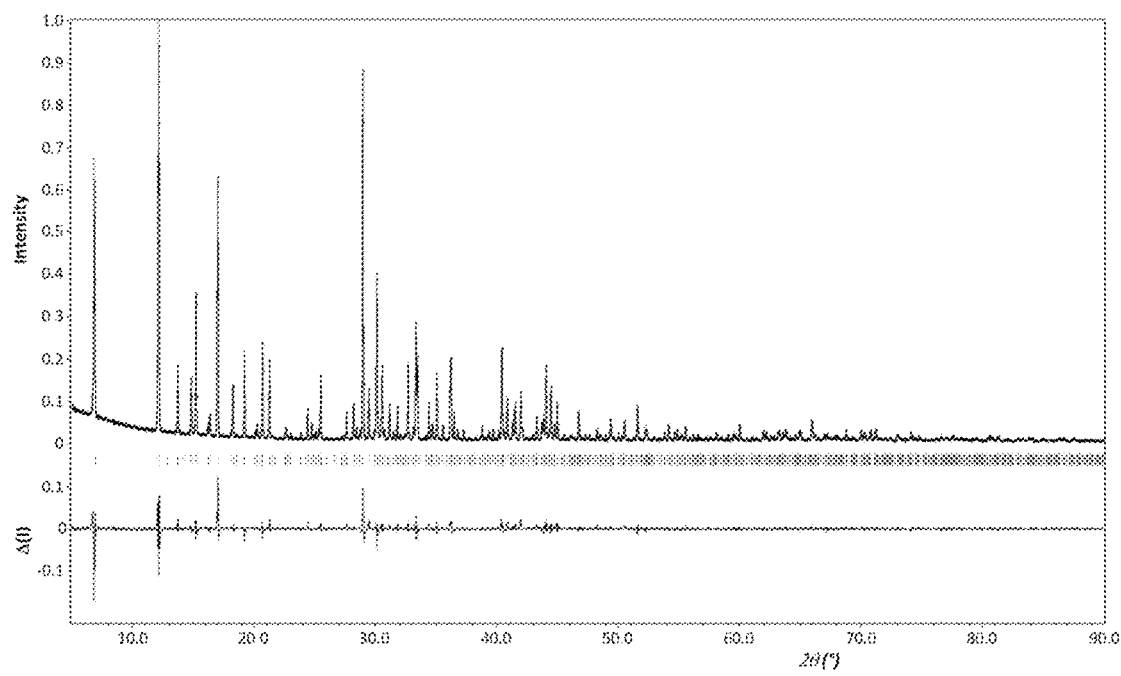
FIG. 4 represents Rietveld refinement for (a) 2D hybrid perovskite (R$_{wp}$=12.41%) and (b) 1D hybrid post-perovskite (R$_{wp}$=24.49%).
Figure 4:
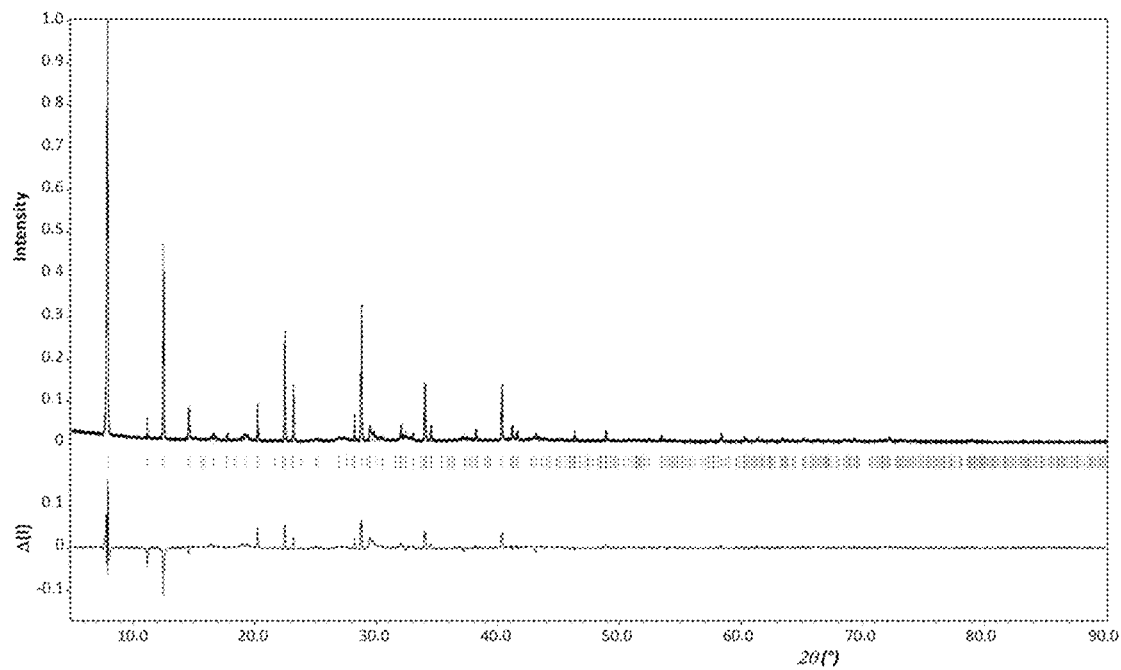

Although such disorder hinders the localization of the organic molecules, a structural model could be proposed. Rietveld refinement was performed (FIG. 4) and showed that the structure is built of lead bromide ladders. Interestingly, this ladder type is directly related to the structure of the post-perovskite which is the high-pressure polymorph of perovskite.

Similarly to the 2D perovskite which derives from perovskite by slicing along (110) planes, the ladder compound derives from post-perovskite by slicing along (100) planes (FIG. 1(a)). Using the same approach to define "low-dimensional hybrid perovskite" from a "hybrid perovskite", the ladder compound is defined as a "low dimensional hybrid post-perovskite", this specific ladder structure can be considered as a low-dimensional post-perovskite.

Solid state NMR experiments were performed to confirm the architecture of the inorganic components. The $^{207}$Pb solid state NMR line is governed by chemical shift (CS) interaction which reflects the electronic environment (EE) of the lead nucleus. The isotropic part of CS corresponds to the position of the line whereas the anisotropic part (CSA) originates from EE anisotropy caused by local distortions of the PbBr$_6$ octahedra. For 2D (110) perovskites, all octahedra share the same EE. Consequently, the $^{207}$Pb MAS NMR spectrum consists in a single line at 180 ppm flanked by spinning side bands (ssb) as shown in FIG. 1(d) for the layered perovskite based on BAPP. For heavy nuclei such as $^{207}$Pb, CS is sensitive to small differences in local structural geometry. Therefore, the broad line exhibited by the $^{207}$Pb NMR spectrum of the one-dimensional post-perovskite based on TDMP (FIG. 1(d)) at the similar isotropic chemical shift than the two-dimensional perovskite based on BAPP and with no significant change in CSA (since no additional ssb appears outside the spectral range initially covered by BAPP compound) is a direct proof of the similar environments of lead (i.e. two terminal bromines in cis position, and four bridging bromines) of the two compounds. The line broadening is a direct consequence of distribution of octahedron geometries around a mean geometry.

Both the 2D perovskite and post-perovskite according to the invention showed high color rendering indexes (CRI of 87, and 75 respectively), which are similar to the ones of previously reported 2D hybrid perovskites [12, 17, 18]. The corresponding correlated color temperatures (CCT) are 4369 K and 7458 K, respectively (FIG. 2(a)). The main difference between the two hybrid lead halides lies on the intensity of the broadband white emission. The PLQY for the layered perovskite was measured at 1.5% which is within the same range as the ones of previously reported compounds [12, 17, 18]. On the other hand, the PLQY of the low-dimensional post-perovskite according to the invention was measured at 45% which is 5-fold of the PLQY of the previous record in hybrid perovskite, and almost 4-fold of the PLQY of the previous record in all lead halides [16, 18].

Figure 2:
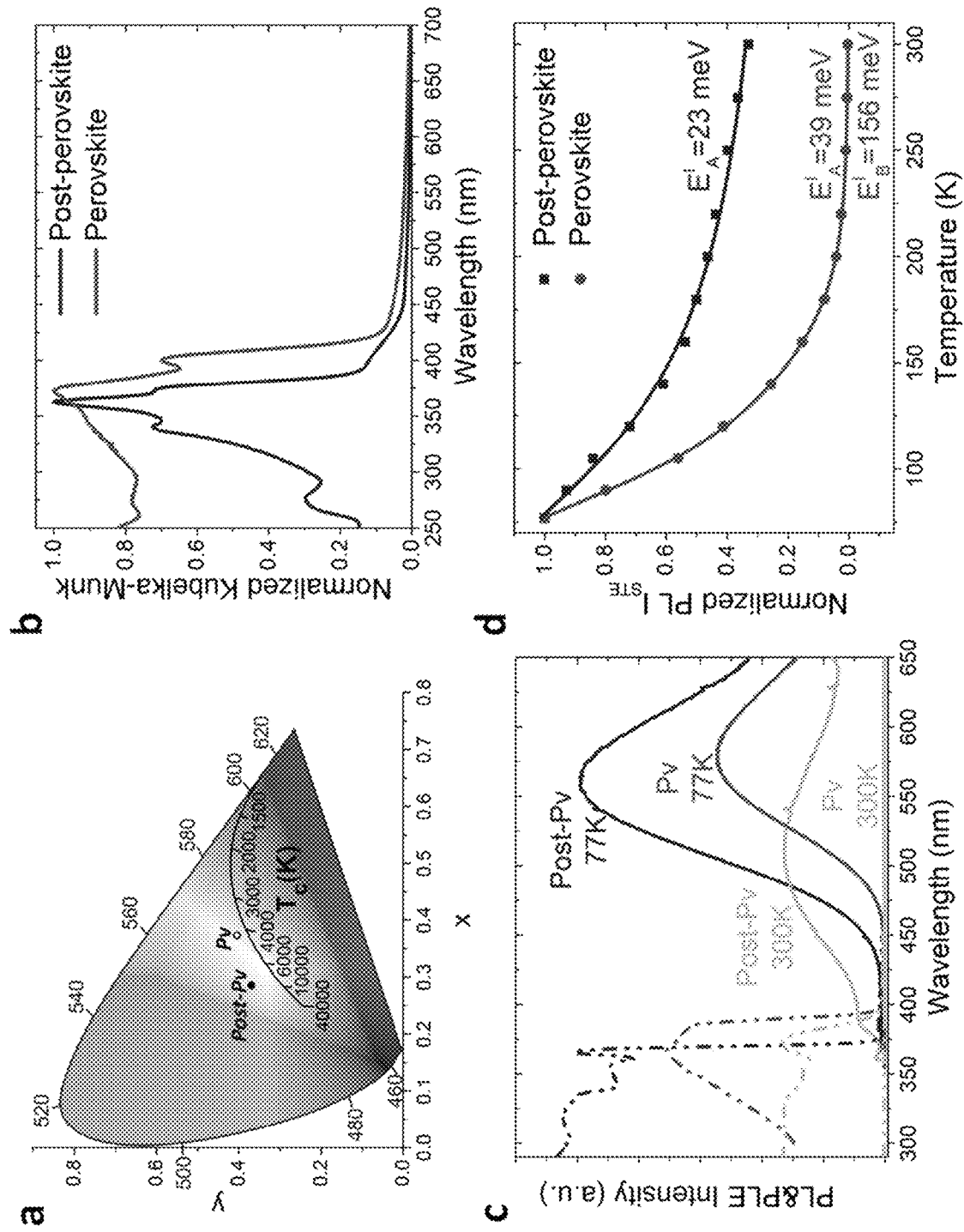
FIG. 2 represents Absorption and Photoluminescence properties of hybrid perovskite and post-perovskite, (a) CIE coordinates of 2D hybrid perovskite (Pv) and 1D hybrid post-perovskite (Post-Pv), (b) Kubelka-Munk absorption spectra, (c) photoluminescence excitation (PLE) and emission (PL) spectra are shown at ambient and liquid nitrogen temperature (PLE: $\lambda_{em}$=582 nm for Pv at 300K, $\lambda_{em}$=510 nm for Post-Pv at 300K, $\lambda_{em}$=582 nm for Pv at 77K, and $\lambda_{em}$=565 nm for Post-Pv at 77K/PL: $\lambda_{exc}$=367 nm for Pv at 300K, $\lambda_{exc}$=330 nm for Post-Pv at 300K, $\lambda_{exc}$=340 nm for Pv at 77K, and $\lambda_{exc}$=330 nm for Post-Pv at 77K), (d) normalized evolution of the intensity of the STE peak (at the maximum emission associated with the STE band) I$_{STE}$ with temperature.
Figure 5:
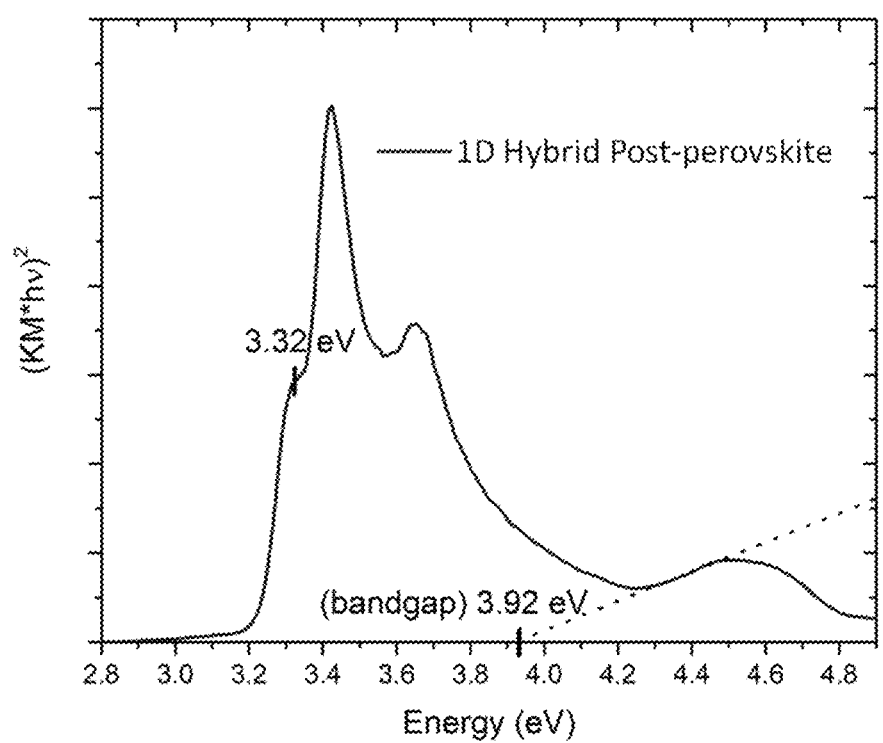
FIG. 5 represents Tauc plot for the hybrid post-perovskite. The bandgap (3.92 eV) corresponds to the intersection of a linear fitting of the band-to-band transition with the zero energy axis. The exciton binding is estimated at 0.60 eV (difference between 3.92 eV and 3.32 eV).
Figure 6:
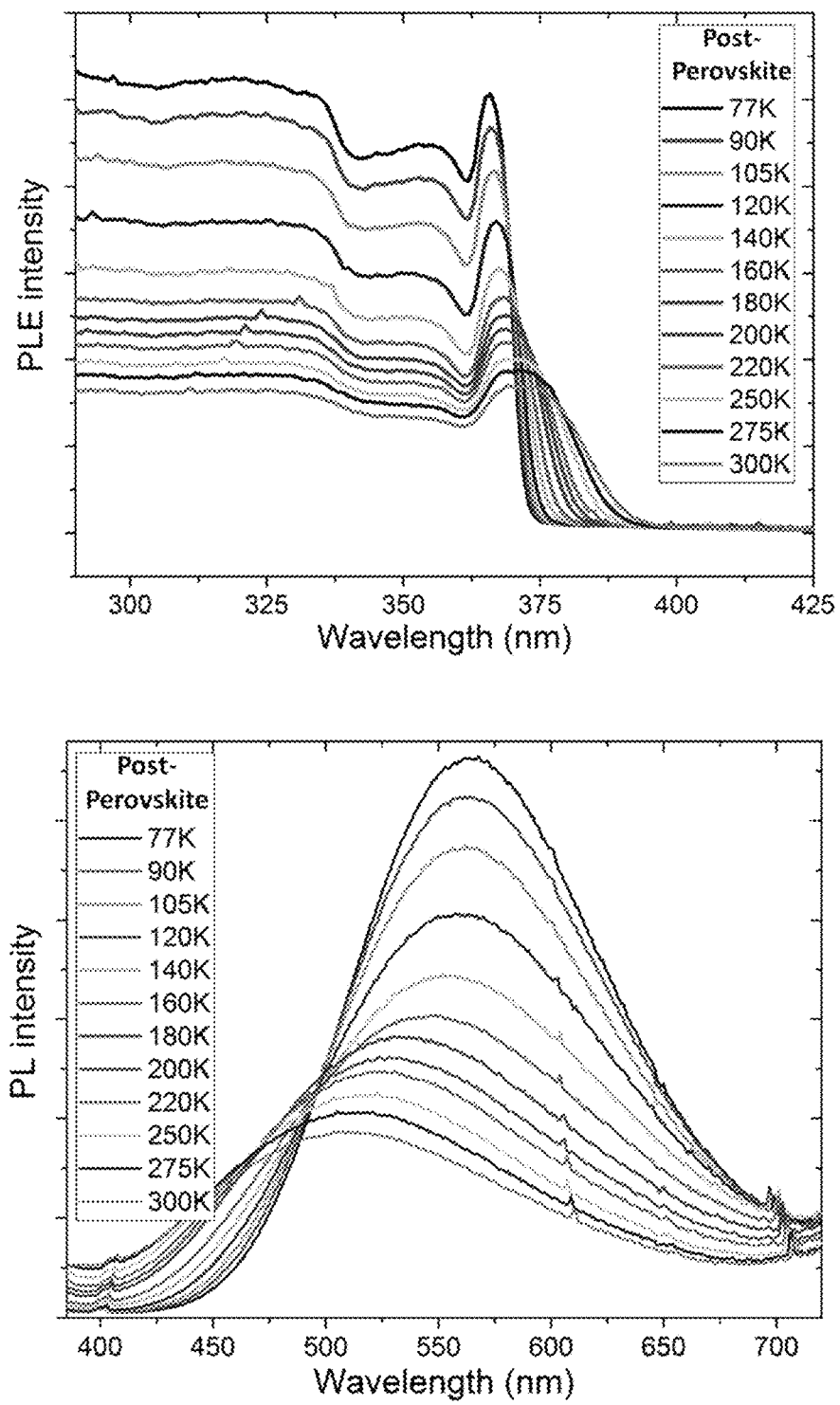
FIG. 6 represents PLE (top) and PL (bottom) spectra for the 1D hybrid post-perovskite at different temperatures. For each excitation (emission) spectra, $\lambda_{em}$ ($\lambda_{exc}$) a were selected to maximize the emission signal.
Figure 7:
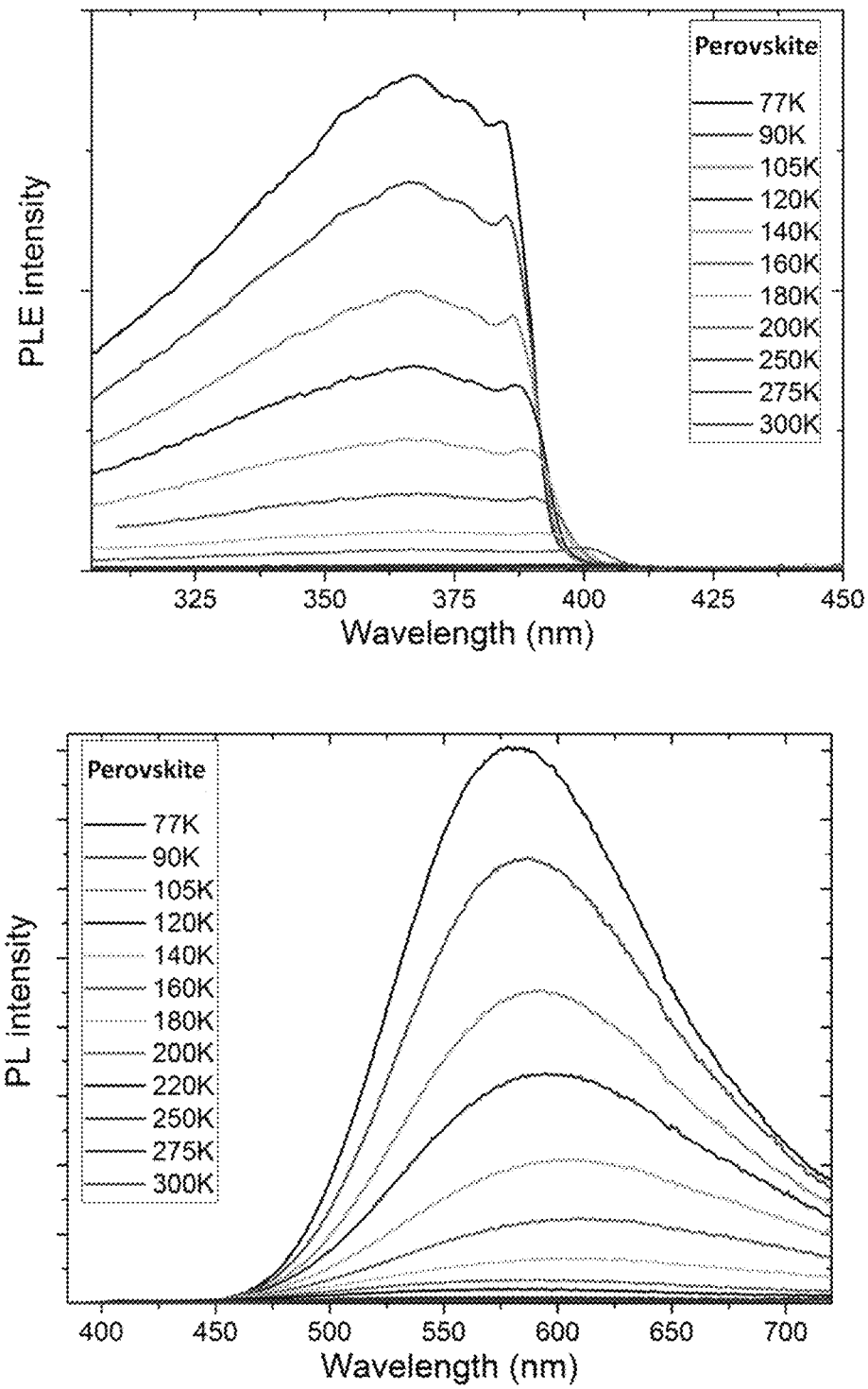
FIG. 7 represents PLE (top) and PL (bottom) spectra for the 2D hybrid perovskite at different temperatures. For each excitation (emission) spectra, $\lambda_{em}$ ($\lambda_{exc}$) a were selected to maximize the emission signal.

Owing to dielectric confinement, sharp excitonic peaks can be observed in Kubelka-Munk absorption spectra (FIG. 2 (b)) and the exciton binding energy is very high (estimated at 600 meV) for the 1D hybrid post-perovskite (FIG. 5) [7, 26-29]. In addition, an Urbach tail below the bandgap shows the formation of localized states (corresponding, for example, to lattice defects/disorder) prior to photoexcitation (FIG. 2 (b)).

Figure 8:
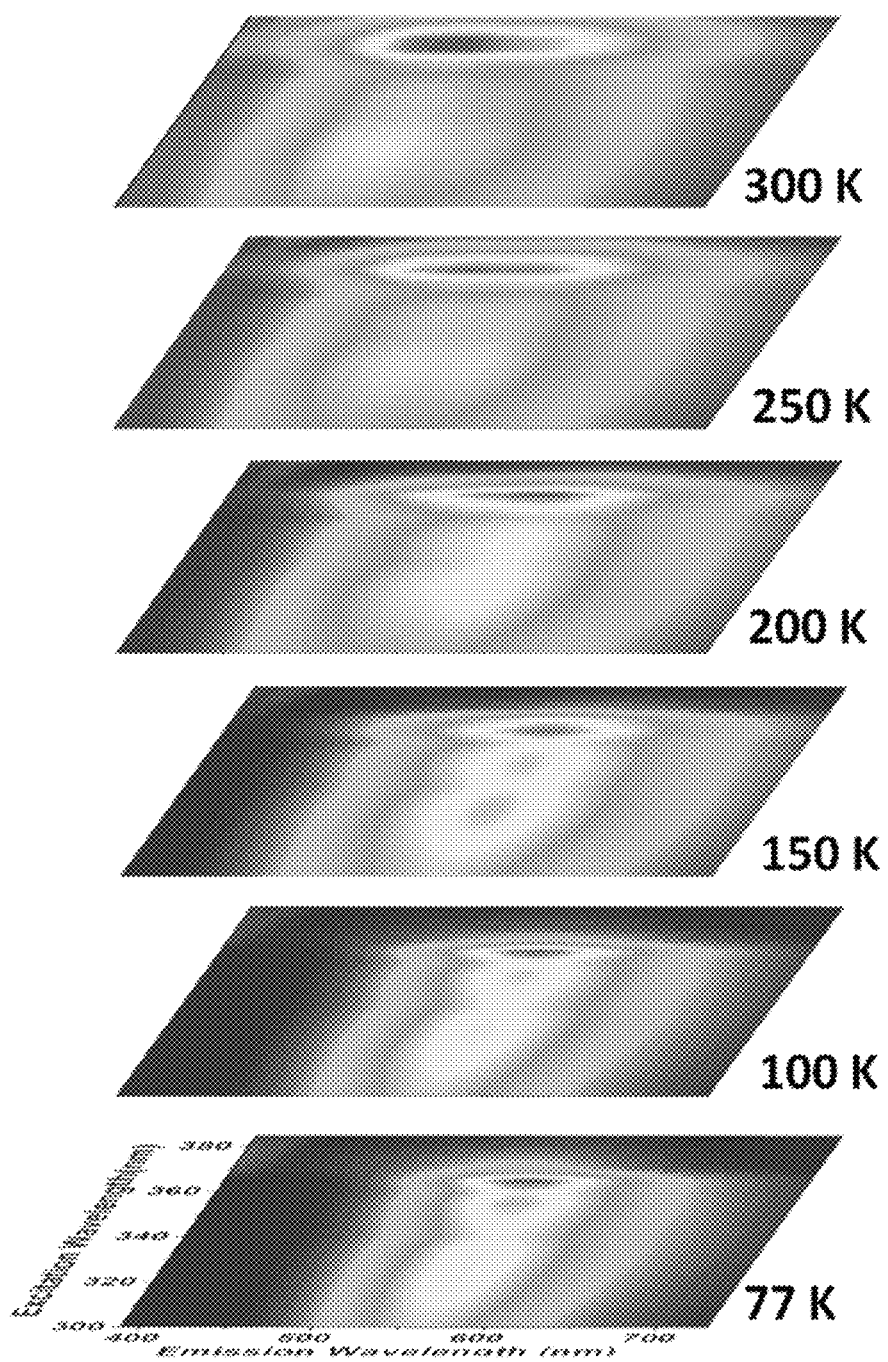
FIG. 8 represents evolution of the photoluminescence properties vs. temperature for the 1D hybrid post-perovskite.

These states favor the trapping of excitons after excitation and could contribute to the enhanced photoluminescence. Hence, locally disordered Pb clusters have previously been shown to have a favorable PL effect on $PbWO_4$ [30]. Photoluminescence spectra at 300K show a broadband emission at 520 nm and a shoulder at 380 nm attributed to the formation of self-trapped exciton (STE) and free exciton (FE), (FIGS. 2 (c), 6 and 7) [17]. While increasing the temperature from 77K to room temperature, both perovskite and post-perovskite show a decrease of the PL intensity together with a blueshift of the broadband emission (FIG. 8).

Figure 9:
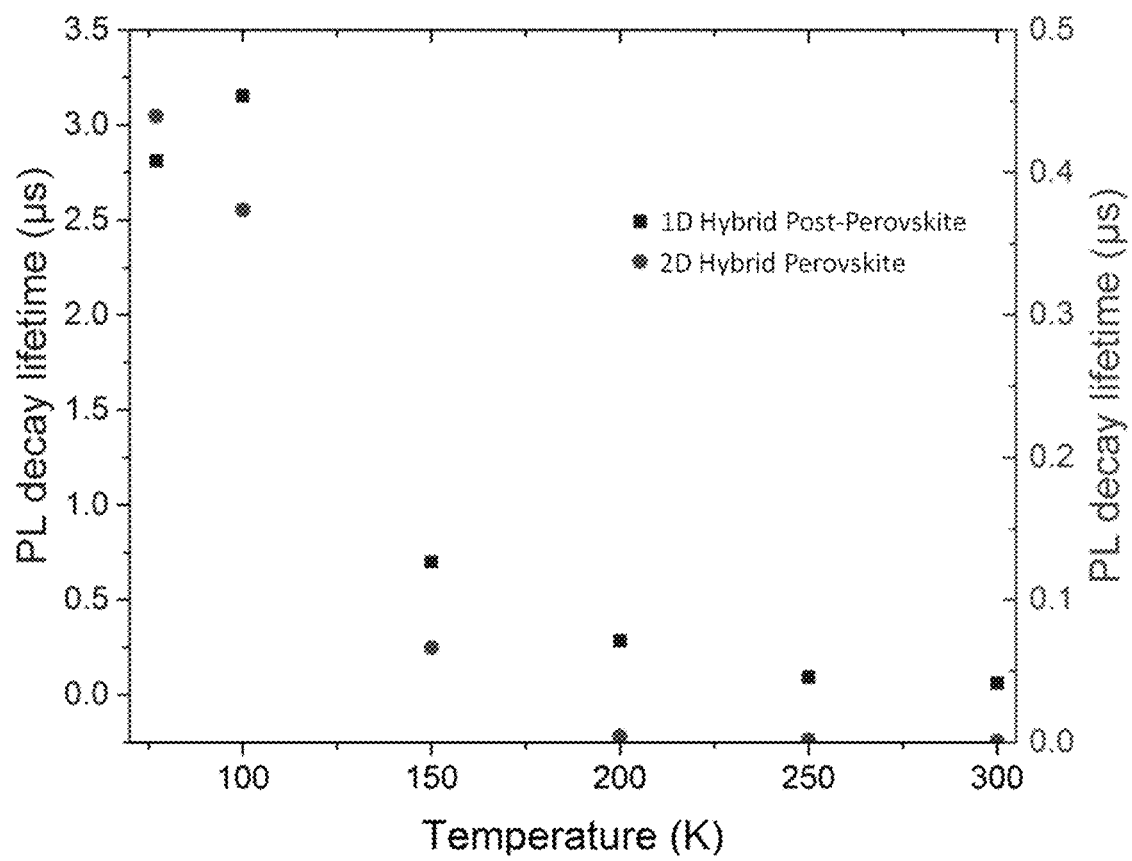
FIG. 9 represents PL decay lifetime vs. temperature for the 2D hybrid perovskite and 1D hybrid post-perovskite.

The evolution of the STE intensity with temperature (FIGS. 2 (d), 6 and 7) clearly reveals the smooth decrease of PL intensity for the hybrid 1D post-perovskite compared to the 2D perovskite. Activation energies E' associated with the process responsible of the decrease of the PL intensity were determined by Arrhenius fitting. $E'_A$ is 23 meV for the 1D post-perovskite while two energies ($E'_A$=39 meV and $E'_B$=156 meV) were determined for the 2D perovskite (Biexponential fitting is necessary for this compound). $E'_A$ (23 meV and 39 meV for 1D and 2D compounds, respectively) are associated with the detrapping process between STE and FE [28]. Beside this, the post-perovskite according to the invention exhibits a very long STE PL lifetime τ of 62 ns at room temperature in comparison to the layered compound (τ=0.58 ns) and the previously reported 2D perovskites (typically lower than 14 ns) [9, 11, 17, 18]. This lifetime, which is sensitive to non-radiative pathways, decreases from 77K to room temperature for both compounds (FIG. 9).

Figure 1:
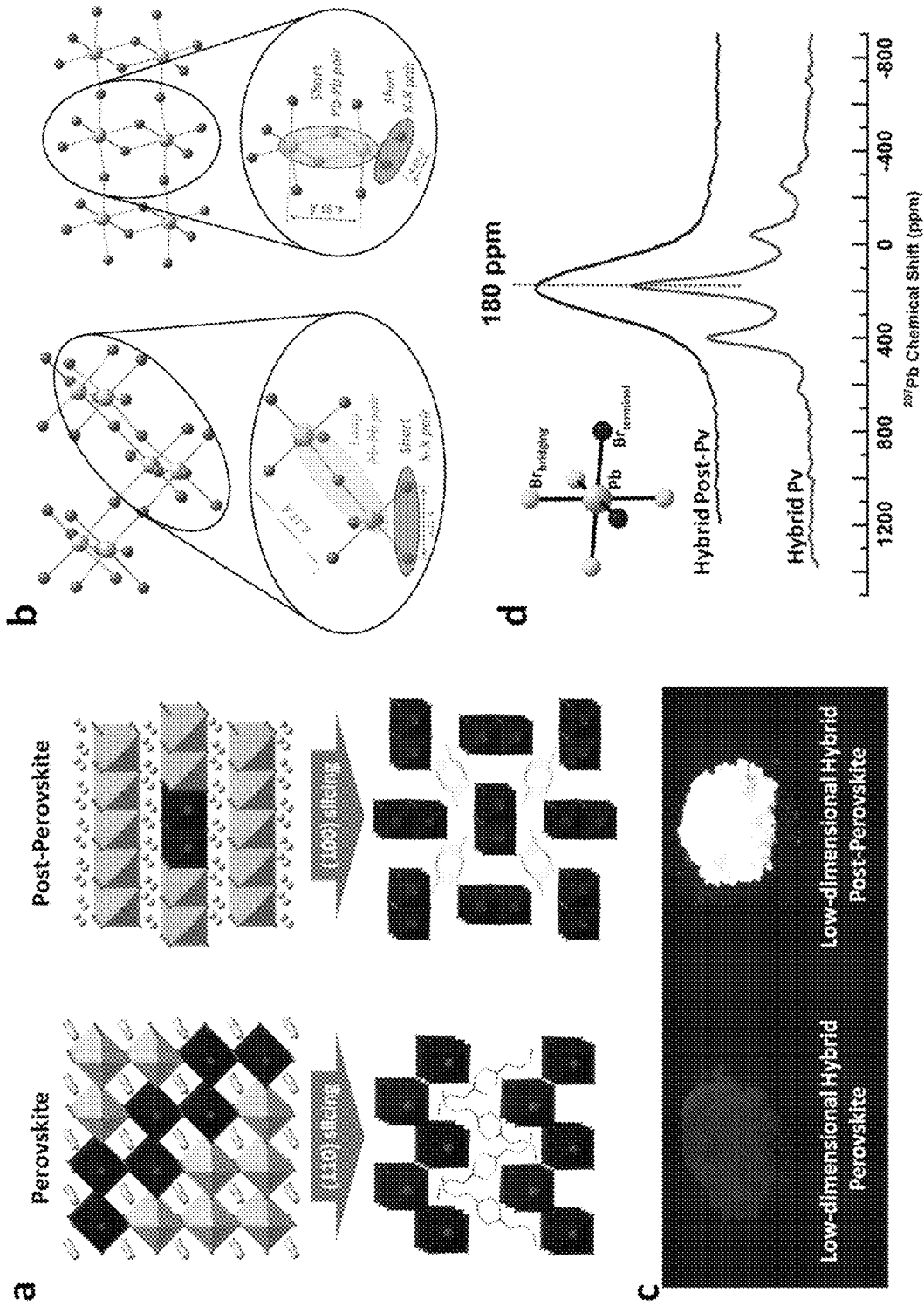
FIG. 1 represents (a) representation of the crystal structures of the two low-dimensional (BAPP)Pb$_2$Br$_8$ and (TDMP)PbBr$_4$ compounds from the parent perovskite (left) and post-perovskite (right), (b) detailed view of the two compounds: in the low-dimensional hybrid post-perovskite, all centres (Pb$_2$$^{3+}$, Pb$_2$$^{2+}$ Pb$^{3+}$, X$_2$$^-$ or X$^{2-}$) are possible owing to short Pb—Pb and X-X pairs, (c) pictures of 2D hybrid perovskite (left) and 1D post-perovskite (right) under UV ($\lambda_{exc}$=365 nm), (d) $^{207}$Pb solid-state MAS (14 kHz) NMR spectra of hybrid perovskite (Pv) and post-perovskite (Post-Pv).

Both the 2D perovskite and 1D post-perovskite exhibit Pb in the same environments (i.e. Pb connected with four bridging bromines and two terminal bromines in cis position) ((FIGS. 1 (b) and (d)). However, 2D perovskites are built of corner-sharing $PbBr_6$ octahedra while the 1D post-perovskites are built of both corner- and edge-sharing octahedra. This structural difference is very important for some radiative species. For corner-sharing $PbX_6$ octahedra, species such as $Pb_2^{3+}$ or $Pb_2^{2+}$ (reported for $PbBr_2$) would be difficult to form under excitation because halogens are located between adjacent Pb [20]. Distortions in perovskites could assist the creation of such species by shortening Pb—Pb distances and increase the intensity of the resulting white emission (PLQY up to 9%) [9, 10, 12, 31]. However, the scale of this distortion is limited by steric effects. At the opposite, such centres are more likely to form when the octahedra share edges because the Pb—Pb distances are significantly shorter. Hence, the shortest Pb—Pb distances are 5.9638(6) Å in the 2D perovskite while they are 4.5494 (64) Å in the 1D post-perovskite. Moreover, each of the dimers (pairs of edge-sharing $PbBr_6$ octahedra) in 1D post-perovskite can act more independently (i.e. without affecting the overall structure) to create species involving Pb pairs and X pairs than in more condensed edge-sharing lead halide structures [16]. The dimensionality of the crystalline systems also plays an important role on the exciton self-trapping. In one-dimensional systems such as the 1D post-perovskite, the deformation energy is low and there is no or small barrier to self-trapping [32]. At the opposite, free states are always stable or metastable in three-dimensional systems [32]. In addition, the excited species are less likely to diffuse throughout the material when the dimensionality decreases. These phenomena would explain why broad-band emissions originating from self-trapped excitons would lead to higher PLQY when the dimensionality of hybrid lead halides is lowered. Thus, lowering the dimensionality is detrimental to solar cells applications in which exciton trapping must be prevented but beneficial in SSL in which it enhances the PLQY.

In addition to these structural characteristics (short Pb—Pb, short X-X, low dimension) which are assets to promote self-trapped states, the PL quenching with temperature must be minimized to enhance the white emission at room temperature. In the 2D perovskite and previously reported hybrid perovskites, the emissions are relatively high at low temperature (i.e. below 100K) but rapidly quench with temperature. The activation energy $E'_B$ associated with this fast PL quenching for the layered compound ($E'_B$=156 meV) and previously reported perovskites (typically around 100-150 meV) are associated with phonon modes from the organic molecules [7, 19, 33]. DFT calculations were performed and enabled to identify these modes as the rocking and twisting of $CH_2$ on chains and cycles (Supporting Information). In the case of the 1D hybrid post-perovskite, Raman spectroscopy, theoretical calculations, and PL techniques suggest that the organic component hardly interacts with the lead halide inorganic component preventing the quenching by the C—H vibrations of TDMP (FIG. 2(d)).

Synthesizing low-dimensional hybrid post-perovskite is an efficient approach to stabilize the self-trapped states. Thus, in addition of tuning the CRI and CCT by halogen substitution which has been extensively investigated in the past few years, the ability of creating such self-trapped states in hybrid lead halides is another important parameter to control the intensity of the white broad-band emission.

Specific characteristics such as low dimensionality of the metal halide system, short Pb—Pb and X-X distances, and weak organic-inorganic interactions favor the formation of such radiative centres by lowering the deformation potentials and preventing the quenching due to the vibration modes of organic molecules. The enhancement of the quantum yield resulting from low dimensional hybrid post-perovskites represents an important step forwards in the practical use of such materials in optoelectronics.

Example 3: Characterization

TABLE 1

Crystallographic data for the 2D hybrid perovskite based on 1,4-Bis(3-aminopropyl)piperazine (BAPP).

| Space group | Pbca |
|---|---|
| a/Å | 8.8256(13) |
| b/Å | 11.9234(10) |
| c/Å | 25.779(4) |
| α/° | 90 |
| β/° | 90 |
| γ/° | 90 |
| Radiation | Mo Kα |
| 2Θ range for data collection/° | 12.92 to 63 |
| Reflections collected | 39548 |
| Data/restraints/parameters | 4458/0/108 |
| Goodness-of-fit on $F^2$ | 1.064 |
| Final R indexes [I >= 2σ (I)] | $R_1$ = 0.0463 w$R_2$ = 0.1066 |
| Largest diff. peak/hole/e Å$^{-3}$ | 2.01/−4.07 |

TABLE 2

Atomic Coordinates (×104) and Equivalent Isotropic Displacement Parameters (Å2 × 103) for the 2D hybrid perovskite.

| Atom | x | y | z | U(eq) |
|---|---|---|---|---|
| Pb1 | 2410.0(3) | 6771.7(2) | 3333.03(10) | 28.81(10) |
| Br1 | 2276.8(10) | 9273.7(6) | 3189.3(4) | 42.3(2) |
| Br2 | 5033.7(11) | 6748.7(8) | 2505.2(4) | 60.4(3) |
| Br3 | 4732.9(13) | 7339.9(9) | 4140.8(4) | 65.8(3) |
| Br4 | 156.4(13) | 6349.3(11) | 4109.2(4) | 70.2(3) |
| C3 | 7028(12) | 4253(11) | 4191(4) | 66(3) |
| N2 | 8921(10) | 4262(8) | 3148(4) | 63(2) |
| C1 | 4466(10) | 4268(8) | 4594(3) | 45(2) |
| C2 | 6633(9) | 5093(8) | 5058(3) | 41.4(18) |
| C4 | 6630(14) | 4510(20) | 3636(5) | 159(11) |
| N1 | 5937(7) | 4893(6) | 4538(2) | 38.8(14) |
| C5 | 7367(15) | 3990(30) | 3247(5) | 132(10) |

TABLE 3

Atomic Coordinates (×10$^4$) and Equivalent Isotropic Displacement Parameters (Å$^2$ × 10$^3$) for the 1D hybrid post-perovskite (TDMP)PbBr$_4$ (with TDMP = Trans-2,5-dimethylpiperazinium) (P-42$_1$m, a = 15.786(2) Å, c = 6.094(12) Å).

| Atom | x | y | z | U(eq) | Occupancy |
|---|---|---|---|---|---|
| Pb1 | 1014.7(15) | 3985.3(15) | 5584(9) | 35.0(9) | 0.645(4) |
| Pb2 | 1014(5) | 3986(5) | 3253(16) | 51(3) | 0.355(4) |
| Br1 | 928(4) | 4072(4) | 560(20) | 45(2) | 0.645(4) |
| Br2 | 980(3) | 5980(3) | 5570(20) | 38.2(16) | 0.645(4) |
| Br3 | 2841(3) | 4033(4) | 5599(18) | 51.8(18) | 0.645(4) |
| Br4 | 952(15) | 4048(15) | 8130(40) | 55(7) | 0.355(4) |
| Br5 | 984(10) | 5984(10) | 3290(40) | 63(6) | 0.355(4) |
| Br6 | 2822(10) | 4031(12) | 3290(30) | 72(5) | 0.355(4) |

The data collection was carried out at 100 K ($R_1$ [I> = 2σ (I)] = 0.0882, w$R_2$ [I> = 2σ (I)] = 0.2200, Goodness-of-fit = 1.022). In this structural model, the organic molecules could not be localized because of strong structural disorder. The refinement of the occupancies was constrained to take in consideration a disorder between two regular PbBr$_6$ octahedra.

Steady-State PL and PLE Vs. Temperature

The two curves of FIG. 2(c) are fitted using the Arrhenius law:

$$I = \frac{I_0}{1 + A\exp(-E_A^I/k_B T)};$$

$$I = \frac{I_0}{1 + A\exp(-E_A^I/k_B T) + B\exp(-E_B^I/k_B T)}$$

Where $I_0$ is the PL intensity at 0K, A (B) is a preexponential factor, $k_B$ the Boltzmann constant and $E_A^I$ ($E_B^I$) the activation energy associated with the process responsible for the decrease of the PL intensity ($E_A^I$=23 meV for the 1D post-perovskite and $E_A^I$=39 meV/$E_B^I$=156 meV for the 2D perovskite). In similar hybrid perovskites, $E_B^I$ as large as 147 meV, 105 meV,[1] 130 meV [39], or 83 meV [40], were previously reported. Thirumal et al. described for their compound two processes associated with two activation energies (see the second equation above): $E_A^I$=12 meV and $E_B^I$=120 meV [41]. The first energy is comparable with $E_A^I$ obtained for the 1D hybrid post-perovskite ($E_A^I$=23 meV) or 2D hybrid perovskite ($E_A^I$=39 meV) while the second one fits well with previous studies and is solely visible in the 2D hybrid perovskite ($E_B^I$=156 meV), in which the PLQYs associated with the broad white light emission were low.

PL Lifetime Vs. Temperature

The mean lifetime τ was obtained by fitting the PL decay with two non-coupled exponentials convoluted with the laser pulse. Table 4 presents the fitting results obtained for the different samples at various temperatures where $\tau_1$, $\tau_2$, $P_1$, $P_2$ are lifetimes and weights for the two non-coupled exponentials.

TABLE 4

Non-coupled biexponential fitting values associated with the PL decay.

| | Samples | | | | | | | | | |
|---|---|---|---|---|---|---|---|---|---|---|
| | Hybrid post-perovskite | | | | | Hybrid perovskite | | | | |
| Temp | $T_1$(ns) | $T_2$(ns) | $P_1$ | $P_2$ | $T_{mean}$ (ns) | $T_1$(ns) | $T_2$(ns) | $P_1$ | $P_2$ | $T_{mean}$ (ns) |
| 77 K | 374 | 3084 | 0.10 | 0.90 | 2813 | 56 | 531 | 0.19 | 0.81 | 441 |
| 100 K | 326 | 3340 | 0.06 | 0.94 | 3159 | 49 | 456 | 0.20 | 0.80 | 375 |
| 150 K | 810 | 191 | 0.82 | 0.18 | 699 | 6.08 | 80 | 0.18 | 0.82 | 67 |
| 200 K | 341 | 50 | 0.80 | 0.20 | 283 | 0.75 | 4.80 | 0.13 | 0.87 | 4.27 |
| 250 K | 18 | 101 | 0.10 | 0.90 | 93 | 1.03 | 2.78 | 0.43 | 0.57 | 2.03 |
| 300 K | 71 | 14 | 0.85 | 0.15 | 62 | 0.58 | 0 | 1 | 0 | 0.58 |

Photoluminescence Quenching with Temperature

Figure 10:
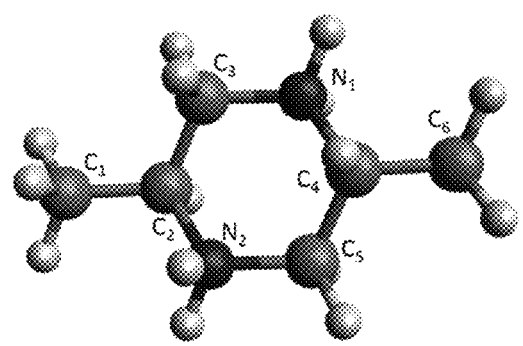
FIG. 10 represents TDMP cation after geometry optimization by DFT calculations
Figure 11:
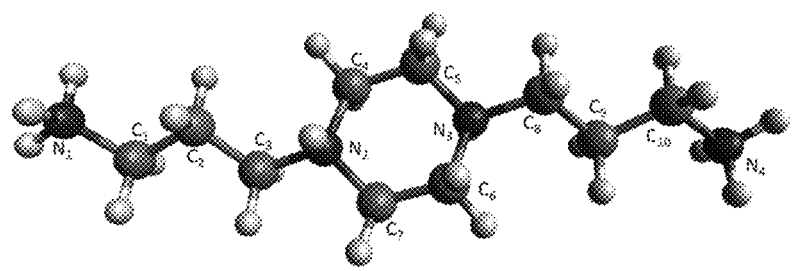
FIG. 11 represents BAPP cation after geometry optimization by DFT calculations

Activation energies $E_B^I$ associated with the process responsible of the Photoluminescence (PL) quenching for the layered compound ($E_B^I$=156 meV) is comparable to previously reported values for other perovskites (typically around 100-150 meV) and can be typically attributed to the organic molecules [38-40]. To identify the group of modes participating to the PL quenching, DFT calculations were performed on both BAPP and TDMP cations. Ground state geometry optimisations and vibrational frequencies were computed at the DFT level using Gaussian 16 Rev. A.03, with the long-range corrected CAM-B3LYP functional associated with the basis set spaug-cc-pvdz [44]. Molecules TDMP (FIG. 10) and BAPP (FIG. 11) are both calculated in vacuum. For both molecules, the calculated bond lengths are in good agreement with experimental bond lengths from the salts (TDMP)$Br_2$ and (BAPP)$Br_4$ (structures determined from Single-crystal X-Ray diffraction data) (Table 5 and 6). From the DFT calculations, vibrational modes of (TDMP)$Br_2$ and post-perovskite (Table 7) as well as (BAPP)$Br_4$ and perovskite (Table 8) could be assigned.

TABLE 5

Bond lengths for TDMP optimized by DFT calculations and the salt (TDMP)$Br_2$.

| Bond | Calculated bond length (Å) | Experimental bond length (Å) in the salt (TDMP)$Br_2$ |
|---|---|---|
| $C_1$—$C_2$ | 1.519 | 1.521 |
| $C_2$—$C_3$ | 1.524 | 1.515 |
| $C_3$—$N_1$ | 1.503 | 1.489 |
| $N_1$—$C_4$ | 1.519 | 1.500 |

TABLE 6

Bond lengths for BAPP in 2D perovskite, BAPP optimized by DFT calculations, and BAPP in (BAPP)Br4.

| Bond | Calculated bond length (Å) | Experimental bond length (Å) in the salt (BAPP)$Br_4$ | Experimental bond length (Å) in BAPP 2D perovskite |
|---|---|---|---|
| $N_1$—$C_1$ | 1.507 | 1.477 | 1.401 |
| $C_1$—$C_2$ | 1.540 | 1.503 | 1.319 |
| $C_2$—$C_3$ | 1.537 | 1.508 | 1.476 |
| $C_3$—$N_2$ | 1.531 | 1.504 | 1.499 |
| $N_2$—$C_4$ | 1.507 | 1.496 | 1.498 |
| $C_4$—$C_5$ | 1.525 | 1.498 | 1.511 |
| $C_5$—$N_3$ | 1.511 | 1.492 | 1.488 |

For the 2D perovskite, the activation energy (156 meV 1258 cm$^{-1}$) corresponding to the major contribution of the PL quenching can be compared with experimental modes obtained in FT-Raman (Region 1100 cm$^{-1}$ to 1400 cm$^{-1}$). The analysis of calculated vibrations allowed to attribute this group of modes to rocking and twisting of $CH_2$ on chains and cycle of the organic molecules. This identification is also consistent with the literature since C—H vibrations acting as luminescence quenchers have previously been identified for other chemical systems [45, 46]. Interestingly, similar activation energies have been previously reported for other low-dimensional hybrid perovskites [38-40]. Thus, it is likely that the PL quenching for other members of this family could also originate from the organic molecules.

TABLE 7

Assignments of vibrational modes (in cm-1) of 1D post-perovskite and the salt (TDMP)$Br_2$. Only bands from the isolated molecules (i.e. above 350 cm$^{-1}$) are addressed.

| Ladder perovskite | (TDMP)$Br_2$ | Principal assignments |
|---|---|---|
| 395 | 399 | C—C—N deformation |
| 465 | 465 | ring deformation |
| 483 | 488 | C—N—C deformation |
| 768 | 771 | ring deformation |
| 820 | 821 | $CH_2$ and $NH_2$ rocking on cycle |
| 959 | 954 | $CH_3$ wagging and C—N stretching |
| 1082 | 1085 | $CH_3$—CH stretching |
| 1131 | 1132 | $CH_3$ wagging and $CH_2$ and $NH_2$ rocking on cycle |
| 1202 | 1201 | $CH_3$ rocking $CH_2$ and $NH_2$ twisting |
| 1215 | 1221 | $CH_3$ and $CH_2$ wagging $NH_2$ twisting |
| 1287 | 1275 | $CH_2$ and $NH_2$ twisting |
| 1349 | 1360 | $CH_3$ wagging $CH_2$ and $NH_2$ twisting |
| 1406 | 1406 | $CH_3$ and $NH_2$ wagging and $CH_2$ twisting |
| 1459 | 1481 | $CH_3$ twisting $CH_2$ wagging |
| 1549 | 1536 | $NH_2$ scissoring |

TABLE 8

Assignments of vibrational modes (in cm$^{-1}$) of 2D perovskite and the salt (BAPP)$Br_4$. Only bands from the isolated molecules (i.e. above 350 cm$^{-1}$) are addressed.

| Layered perovskite | (BAPP)$Br_4$ | Principal assignments |
|---|---|---|
| 471 | 467 | C—N—C deformation on cycle and C—C—N deformation and chains |
| 500 | 491 | C—C—N deformation on cycle and on chains |
| 523 | 535 | — |
| 747 | 768 | $CH_2$ rocking on chains |
| 796 | 786 | $CH_2$ rocking on chains and ring deformation |
| 813 | 812 | $CH_2$ rocking on cycle |
| 827 | 829 | $CH_2$ twisting and rocking and NH3 twisting |
| 891 | 891 | C—N stretching and NH3 twisting |
| 1049 | 1044 | C—C stretching on chains |
| 1089 | 1077 | $CH_2$ rocking on cycle and twisting $CH_2$ on chains and NH3 wagging |
| 1183 | 1175 | $CH_2$ and NH twisting on cycle |
| 1262 | 1260 | $CH_2$ twisting on chains and NH deformation on cycle |
| 1327 | 1308 | $CH_2$ twisting on cycle and chains |
| 1433 | 1446 | $CH_2$ wagging on chains and $CH_2$ scissoring on cycle and N—H deformation on cycle |
| 1473 | 1478 | $CH_2$ scissoring on cycle and chains |
| 1564 | 1541 | NH3 wagging |
| 1588 | 1617 | NH3 scissoring and twisting |

From these attributions of the vibration modes responsible of the PL quenching with temperature, two hypotheses could explain why the 2D perovksite shows the contribution of C—H vibrations to the PL quenching which remains unobserved for the 1D post-perovskite:

(1) The vibration modes (rocking and twisting of $CH_2$) of BAPP are (de)activated with temperature and always deactivated for TDMP.

(2) The non-radiative transfer is temperature dependant and is influenced by organic-inorganic interactions.

Figure 12:
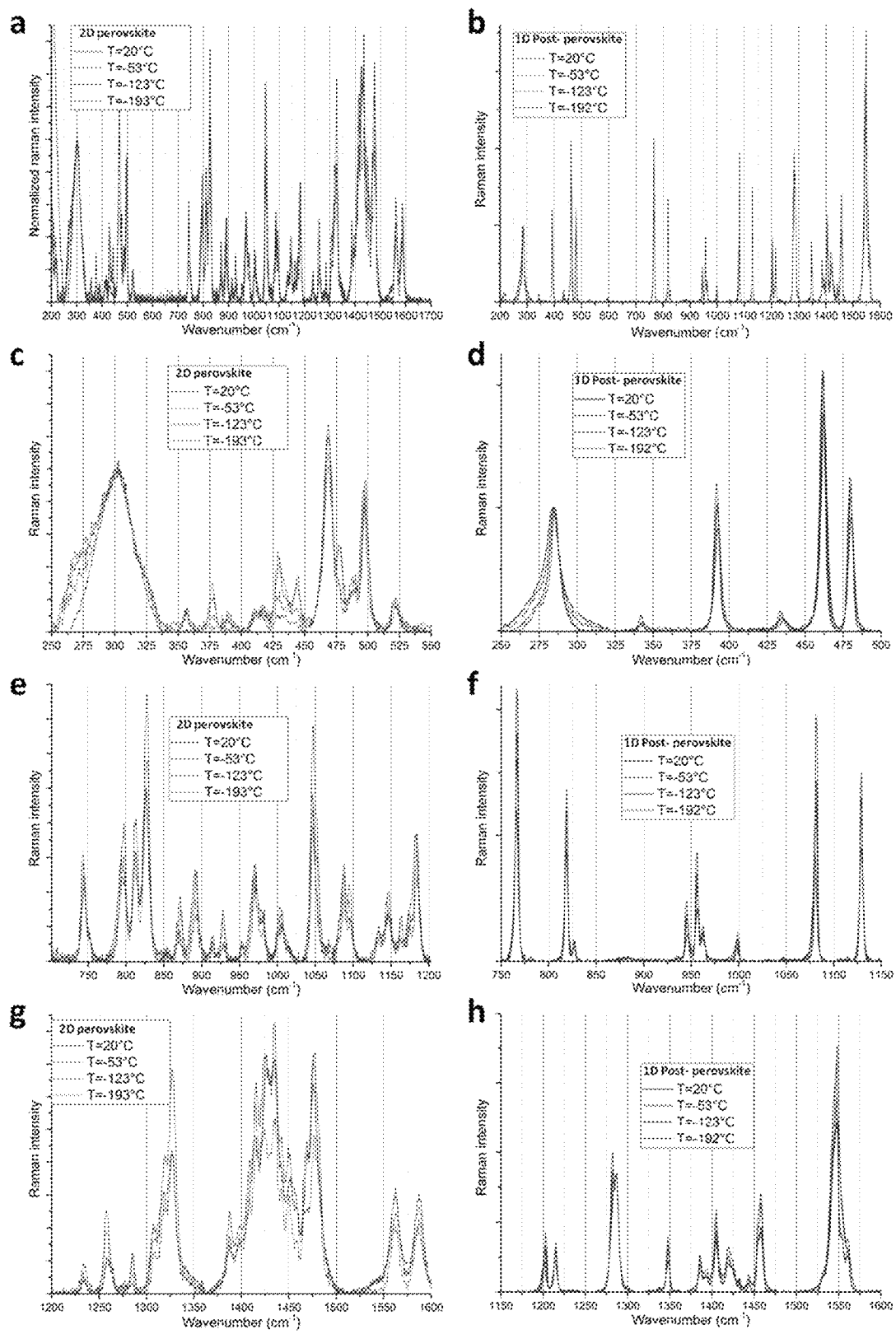
FIG. 12 represents Temperature dependant Raman spectra (Laser wavelength excitation: 512 nm) of (a) 2D perovskite from 200 cm$^{-1}$ to 1700 cm$^{-1}$, (b) 1D post-perovskite from 200 cm$^{-1}$ to 1700 cm$^{-1}$, (c) 2D perovskite from 250 cm$^{-1}$ to 550 cm$^{-1}$, (d) 1D post-perovskite from 250 cm$^{-1}$ to 500 cm$^{-1}$, (e) 2D perovskite from 700 cm$^{-1}$ to 1200 cm$^{-1}$, (f) 1D post-perovskite from 750 cm$^{-1}$ to 1150 cm$^{-1}$, (g) 2D perovskite from 1200 cm$^{-1}$ to 1600 cm$^{-1}$, (h) 1D post-perovskite from 1150 cm$^{-1}$ to 1600 cm$^{-1}$. All spectra have been background subtracted and normalized to the band located at 303 cm$^{-1}$ and 286 cm$^{-1}$ for the 2D perovskite (BAPP molecule) and 1D post-perovskite (TDMP molecule), respectively.

To discriminate between hypotheses (1) and (2) of the PL quenching, complete Raman spectra of 1D post-perovskite and 2D perovskite have been collected vs. temperature (between 200 cm$^{-1}$ to 1700 cm$^{-1}$) (FIG. 12). From these measurements, no specific mode (or group of modes) is identified as being deactivated from low to room temperature. This observation is consistent with the nature of the modes involved in the PL quenching since there is no reason for which the C—H vibrations would be deactivated in the case of TDMP. Thus, hypothesis (1) is unlikely.

Figure 13:
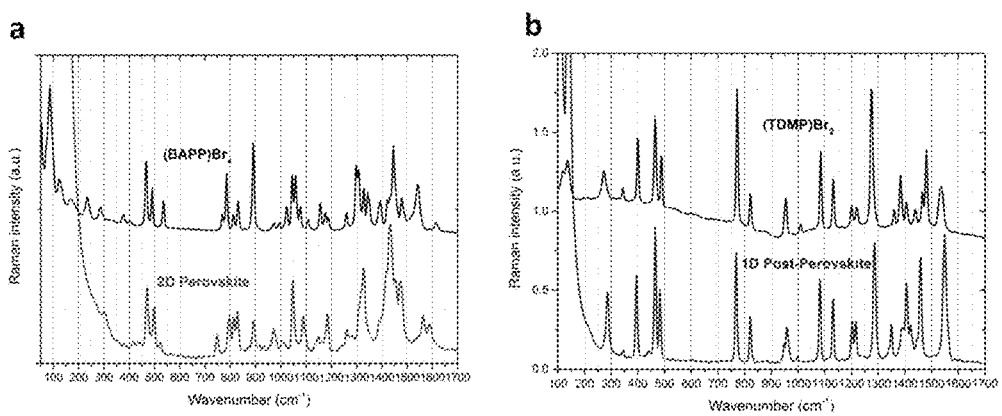
FIG. 13 represents Raman spectra of (a) 2D hybrid perovskite compared with (BAPP)Br$_4$, (b) 1D post-perovskite compared with (TDMP)Br$_2$.

To confirm the hypothesis (2) and better understand the differences in the organic-inorganic interactions of post-perovskite vs. perovskite, further analyses of the Raman spectra and DFT calculations have been carried out. The comparison between spectra of these compounds vs. salts can provide information on the interactions of organic molecules with inorganic lead halide networks. Thus, the spectrum of the 2D perovskite show some discrepancies with the salt (BAPP)Br$_4$ (relatively large band shifts and some differences in band intensities) (FIG. 13(a)) whereas a good agreement can be observed between spectra of the 1D post-perovskite with (TDMP)Br$_2$ (small band shifts and variations of intensities) (FIG. 13(b)). This comparison indicates a strong interaction between the inorganic 2D perovskite and the BAPP molecules [47, 48], while the inorganic 1D post-perovskite hardly interacts with TDMP molecules. Such observation is further confirmed by the analysis of bond lengths (Table 6). Thus, for BAPP cation, bond lengths are well estimated by DFT for the piperazine cycle. However, bond lengths corresponding to the alkyl groups are much shorter in the 2D perovskite than in the calculated isolated molecule. Such differences are due to the constraints of the inorganic layers on the organic chains (organic chains of BAPP are in the cavities of the (110) layers).

In summary, this analysis reveals weak interactions between TDMP and post-perovskite network which prevents the luminescence quenching for this compound. For the perovskite network, close proximity with the confined alkyl chains of BAPP favors the thermal quenching by C—H vibrations. This investigation is also supported by X-ray diffraction data which shows that BAPP is well-ordered and confined inside the cavities of the (110) 2D perovskites. In contrast, TDMP is not constrained by the inorganic post-perovskite network as suggested by the disorder observed by X-ray diffraction.

LIST OF REFERENCES

1. Tan, Z.-K. et al. Bright light-emitting diodes based on organometal halide perovskite. *Nat. Nanotechnol.* 9, 687-692 (2014).
2. Sutherland, B. R. & Sargent, E. H. Perovskite photonic sources. *Nat. Photonics* 10, 295-302 (2016).
3. Stranks, S. D. & Snaith, H. J. Metal-halide perovskites for photovoltaic and light-emitting devices. *Nat. Nanotechnol.* 10, 391-402 (2015).
4. Nie, W. et al. High-efficiency solution-processed perovskite solar cells with millimeter-scale grains. *Science* 347, 522-525 (2015).
5. Tsai, H. et al. High-efficiency two-dimensional Ruddlesden-Popper perovskite solar cells. *Nature* 536, 312-316 (2016).
6. Yuan, M. et al. Perovskite energy funnels for efficient light-emitting diodes. *Nat. Nanotechnol.* 11, 872-877 (2016).
7. Blancon, J.-C. et al. Extremely efficient internal exciton dissociation through edge states in layered 2D perovskites. *Science* eaal4211 (2017). doi:10.1126/science.aa14211
8. Dohner, E. R., Hoke, E. T. & Karunadasa, H. I. Self-Assembly of Broadband White-Light Emitters. *J. Am. Chem. Soc.* 136, 1718-1721 (2014).
9. Dohner, E. R., Jaffe, A., Bradshaw, L. R. & Karunadasa, H. I. Intrinsic White-Light Emission from Layered Hybrid Perovskites. *J. Am. Chem. Soc.* 136, 13154-13157 (2014).
10. Cortecchia, D. et al. *Broadband Emission in Two-Dimensional* Hybrid Perovskites: The Role of Structural Deformation. *J. Am. Chem. Soc.* 139, 39-42 (2017).
11. Thirumal, K. et al. Morphology-Independent Stable White-Light Emission from Self-Assembled Two-Dimensional Perovskites Driven by Strong Exciton-Phonon Coupling to the Organic Framework. *Chem. Mater.* 29, 3947-3953 (2017).
12. Mao, L., Wu, Y., Stoumpos, C. C., Wasielewski, M. R. & Kanatzidis, M. G. White-Light Emission and Structural Distortion in New Corrugated Two-Dimensional Lead Bromide Perovskites. *J. Am. Chem. Soc.* 139, 5210-5215 (2017).
13. Zhuang, Z. et al. Intrinsic Broadband White-Light Emission from Ultrastable, Cationic Lead Halide Layered Materials. *Angew. Chem.* 129, 14603-14608 (2017).
14. Shi, D. et al. Low trap-state density and long carrier diffusion in organolead trihalide perovskite single crystals. *Science* 347, 519-522 (2015).
15. Wu, X. et al. Trap States in Lead Iodide Perovskites. *J. Am. Chem. Soc.* 137, 2089-2096 (2015).
16. Yuan, Z. et al. One-dimensional organic lead halide perovskites with efficient bluish white-light emission. *Nat. Commun.* 8, 14051 (2017).
17. Hu, T. et al. Mechanism for Broadband White-Light Emission from Two-Dimensional (110) Hybrid Perovskites. *J. Phys. Chem. Lett.* 7, 2258-2263 (2016).
18. Yin, J., Li, H., Cortecchia, D., Soci, C. & Brédas, J.-L. Excitonic and Polaronic Properties of 2D Hybrid Organic-Inorganic Perovskites. *ACS Energy Lett.* 2, 417-423 (2017).
19. Cortecchia, D. et al. Polaron self-localization in white-light emitting hybrid perovskites. *J. Mater. Chem. C* 5, 2771-2780 (2017).
20. de Gruijter, W. C. & Kerssen, J. EPR and luminescence of u.v. irradiated PbCl$_2$ and PbBr$_2$ crystals. *Solid State Commun.* 10, 837-841 (1972).
21. Iwanaga, M., Watanabe, M. & Hayashi, T. Charge separation of excitons and the radiative recombination process in PbBr$_2$ crystals. *Phys. Rev. B* 62, 10766-10773 (2000).
22. Mitzi, D. B., Wang, S., Feild, C. A., Chess, C. A. & Guloy, A. M. Conducting Layered Organic-inorganic Halides Containing <110>-Oriented Perovskite Sheets. *Science* 267, 1473-1476 (1995).
23. Li, Y. Y. et al. Novel (110)-Oriented Organic-Inorganic Perovskite Compound Stabilized by N-(3-Aminopropyl) imidazole with Improved Optical Properties. *Chem. Mater.* 18, 3463-3469 (2006).
24. Takeoka, Y., Asai, K., Rikukawa, M. & Sanui, K. Hydrothermal Synthesis and Structure of Zero-dimensional Organic-inorganic Perovskites. *Chem. Lett.* 34, 602-603 (2005).
25. Tulsky, E. G. & Long, J. R. Dimensional Reduction: A Practical Formalism for Manipulating Solid Structures. *Chem. Mater.* 13, 1149-1166 (2001).
26. Liao, W.-Q. et al. A lead-halide perovskite molecular ferroelectric semiconductor. *Nat. Commun.* 6, 8338 (2015).
27. Saidaminov, M. I. et al. High-quality bulk hybrid perovskite single crystals within minutes by inverse temperature crystallization. *Nat. Commun.* 6, 8586 (2015).

28. Zhang, Z., Wang, M., Ren, L. & Jin, K. Tunability of Band Gap and Photoluminescence in $CH_3NH_3PbI_3$ Films by Anodized Aluminum Oxide Templates. *Sci. Rep.* 7, 1918 (2017).
29. A. Leguy, A. M. et al. Experimental and theoretical optical properties of methylammonium lead halide perovskites. *Nanoscale* 8, 6317-6327 (2016).
30. Anicete-Santos, M. et al. Contribution of structural order-disorder to the green photoluminescence of $PbWO_4$. *Phys. Rev. B* 75, 165105 (2007).
31. Smith, M. D., Jaffe, A., Dohner, E. R., Lindenberg, A. & Karunadasa, H. I. Structural Origins of Broadband Emission from Layered Pb—Br Hybrid Perovskites. *Chem. Sci.* 8, 4497-4504 (2017).
32. Song, K. S. & Williams, R. T. *Self-Trapped Excitons*. (Springer-Verlag, 1993).
33. Yangui, A. et al. Optical Investigation of Broadband White-Light Emission in Self-Assembled Organic-Inorganic Perovskite $(C_6H_{11}NH_3)_2PbBr_4$. *J. Phys. Chem. C* 119, 23638-23647 (2015).
34. Handbook of Crystal Growth (Second Edition). in (ed. Nishinaga, T.) iii (Elsevier, 2015). doi:10.1016/B978-0-444-56369-9.01001-7
35. Authier, A. *International Tables for Crystallography* 2nd edn, Vol. D, Ch. A.A (Wiley, 2013).
36. Chayen, N. E. & Saridakis, E. Protein crystallization: from purified protein to diffraction-quality crystal. *Nat. Methods* 5, 147-153 (2008).
37. de Mello, J. C., Wittmann, H. F. & Friend, R. H. An improved experimental determination of external photoluminescence quantum efficiency. *Adv. Mater.* 9, 230-232 (1997).
38. Cortecchia, D. et al. Polaron self-localization in white-light emitting hybrid perovskites. *J. Mater. Chem. C* 5, 2771-2780 (2017).
39. Blancon, J.-C. et al. Extremely efficient internal exciton dissociation through edge states in layered 2D perovskites. *Science eaal4211* (2017). doi:10.1126/science.aal4211
40. Yangui, A. et al. Optical Investigation of Broadband White-Light Emission in Self-Assembled Organic-Inorganic Perovskite $(C_6H_{11}NH_3)_2PbBr_4$. *J. Phys. Chem. C* 119, 23638-23647 (2015).
41. Thirumal, K. et al. Morphology-Independent Stable White-Light Emission from Self-Assembled Two-Dimensional Perovskites Driven by Strong Exciton-Phonon Coupling to the Organic Framework. *Chem. Mater.* 29, 3947-3953 (2017).
42. Massuyeau, F. et al. Electronic interaction in composites of a conjugated polymer and carbon nanotubes: first-principles calculation and photophysical approaches. *Beilstein J. Nanotechnol.* 6, 1138-1144 (2015).
43. Frisch, M. et al. Gaussian, Inc., Wallingford CT, 2016. Gaussian G16A03.2016.
44. Yanai, T., Tew, D. P. & Handy, N. C. A new hybrid exchange-correlation functional using the Coulomb-attenuating method (CAM-B3LYP). *Chem. Phys. Lett.* 393, 51-57 (2004).
45. Wolbers, M. P. O. et al. Photophysical studies of m-terphenyl-sensitized visible and near-infrared emission from organic 1:1 lanthanide ion complexes in methanol solutions. *J. Chem. Soc. Perkin Trans. II* 1998, 2141-2150 (1998).
46. Bischof, C., Wahsner, J., Scholten, J., Trosien, S. & Seitz, M. Quantification of C—H Quenching in Near-IR Luminescent Ytterbium and Neodymium Cryptates. *J. Am. Chem. Soc.* 132, 14334-14335 (2010).
47. Cortecchia, D. et al. Broadband Emission in Two-Dimensional Hybrid Perovskites: The Role of Structural Deformation. *J. Am. Chem. Soc.* 139, 39-42 (2017).
48. Xie, L.-Q. et al. Organic-inorganic interactions of single crystalline organolead halide perovskites studied by Raman spectroscopy. *Phys. Chem. Chem. Phys.* 18, 18112-18118 (2016).
49. Dobson, D. P. et al. Towards better analogues for $MgSiO_3$ post-perovskite: $NaCoF_3$ and $NaNiF_3$, two new recoverable fluoride post-perovskites. *Physics of the Earth and Planetary Interiors*, 189, 3-4, 171-175 (2011).
50. Wang, S.-S. et al. Temperature-Induced Structural Phase Transitions in Two New Postperovskite Coordination Polymers. *Crystal Growth & Design*, 19, 2, 1111-1117 (2019).

The invention claimed is:

1. A one dimensional hybrid post-perovskite of formula I:

$$A_a M_m X_x, y H_2O \quad \text{Formula I}$$

wherein
a=1,
m=1,
x=4,
0≤y,
A represents a cis- or trans-piperazine of formula II:

$$\text{Formula II}$$

in which $R^1$ and $R^2$, identical or different, represent a $C_1$-$C_3$ linear or branched alkyl chain,
M represents one or more metal atoms chosen from the group consisting of Pb, Sn, Ge, Sb, Bi, Mn and Zn and mixture thereof,
X represents one or more halogen atoms.

2. The one dimensional hybrid post-perovskite according to claim 1, wherein A represents trans-2,5-dimethylpiperazine.

3. The one dimensional hybrid post-perovskite according to claim 1, wherein X is chosen from F, Cl, Br and I and mixtures thereof.

4. The one dimensional hybrid post-perovskite according to claim 1, wherein M is chosen from Pb and Sn.

5. A method for producing the one dimensional hybrid post-perovskite of claim 1, comprising a step of mixing the reagents:
one or more M or $MX_2$,
a piperazine, and
one or more aqueous HX to obtain an aqueous mixture,
the piperazine, M and X being defined as above.

6. The method according to claim 5, further comprising a step of heating and agitating the mixture.

7. The method according to claim 6, wherein the heating temperature is from 20° C. to 250° C.

8. The method according to claim 6, wherein the agitation is carried over a period from 10 seconds to 100 hours.

9. A luminescent material comprising a one dimensional hybrid post-perovskite according to claim 1.

10. A luminescent device comprising a one dimensional hybrid post-perovskite material according to claim 9.

11. A one dimensional hybrid post-perovskite $TDMPPbBr_4$ crystal form wherein the XRPD pattern at Bragg angles (2θ) shows peaks of values 7.92°, 12.52°, 14.60°, 20.24°, 22.50°, 23.20°, 28.22°, 28.80°, wherein TDMP stands for trans-2,5-dimethylpiperazine.

12. A one dimensional hybrid post-perovskite TDMPPbCl$_4$ crystal form wherein the XRPD pattern at Bragg angles (2θ) shows peaks of values 8.15°, 12.86°, 18.18°, 20.74°, 23.02°, 23.75°, 28.87°, 29.45°, 32.75°, 33.78°, 34.78°, 35.28°, wherein TDMP stands for trans-2,5-dimethylpiperazine.

13. A one dimensional hybrid post-perovskite TDMPPbI$_4$ crystal form wherein the XRPD pattern at Bragg angles (2θ) shows peaks of values 7.68°, 12.13°, 13.73°, 21.74°, 22.42°, 27.79°, 32.83°, wherein TDMP stands for trans-2,5-dimethylpiperazine.

14. The one dimensional hybrid post-perovskite according to claim 1, configured for a luminescent device comprising a LED including display or backlighting, LASER, wireless light fidelity.

15. The method according to claim 7, wherein the agitation is carried over a period from 10 seconds to 100 hours.

16. The one dimensional hybrid post-perovskite according to claim 1, wherein A represents a cis- or trans-piperazine of formula II in which R$^1$ and R$^2$ represent methyl groups.

17. The one dimensional hybrid post-perovskite according to claim 1, wherein M is a mixture of metals M$^1$ and M$^2$, wherein M$^1$ and M$^2$ are different and represents each one metal atom chosen from the group consisting of Pb, Sn, Ge, Sb, Bi, Mn and Zn and mixture thereof.

18. The one dimensional hybrid post-perovskite according to claim 17, wherein, in formula I, M$_m$ represents M$^1_{m1}$M$^2_{m2}$, wherein 0<m1<1, 0<m2<1 and m1+m2=m=1.

19. The one dimensional hybrid post-perovskite according to claim 18, wherein m1 is in a range from 0.9000 to 0.9999 and wherein m2 is in a range from 0.0001 to 0.1000.

20. The one dimensional hybrid post-perovskite according to claim 17, wherein M$^1$ is Pb or Sn and wherein M$^2$ is Mn.

21. The luminescent device according to claim 10, wherein the luminescent device comprises at least one LED.

22. The luminescent device according to claim 10, wherein the luminescent device is chosen from the group consisting of a display, a backlighting unit, a LASER, a wireless light fidelity and a large area display.

23. A one dimensional hybrid post-perovskite TDMPPb$_{0.9997}$Mn$_{0.0003}$Br$_4$ crystal form wherein the XRPD pattern at Bragg angles (2θ) shows peaks of values 8.10°, 12.71°, 20.45°, 22.68°, 23.40°, 28.40°, 28.98°, wherein TDMP stands for trans-2,5-dimethylpiperazine.

* * * * *